(12) United States Patent
Takada et al.

(10) Patent No.: US 8,253,130 B2
(45) Date of Patent: Aug. 28, 2012

(54) ORGANIC ELECTROLUMINESCENCE DEVICE

(75) Inventors: Saki Takada, Kanagawa (JP); Toshihiro Ise, Kanagawa (JP); Yosuke Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 71 days.

(21) Appl. No.: 12/894,354

(22) Filed: Sep. 30, 2010

(65) Prior Publication Data

US 2011/0073848 A1 Mar. 31, 2011

(30) Foreign Application Priority Data

Sep. 30, 2009 (JP) ................................. 2009-228685
Jan. 28, 2010 (JP) ................................. 2010-017478

(51) Int. Cl.
*H01L 29/08* (2006.01)
(52) U.S. Cl. ............... 257/40; 438/99; 428/690
(58) Field of Classification Search .................... 257/40; 438/99; 428/690
See application file for complete search history.

(56) References Cited

U.S. PATENT DOCUMENTS

| | | | | |
|---|---|---|---|---|
| 7,348,070 B2 * | 3/2008 | Ise et al. | ......................... | 428/690 |
| 7,501,190 B2 * | 3/2009 | Ise | .................. | 428/690 |
| 7,981,524 B2 * | 7/2011 | Ise et al. | ........................ | 428/690 |
| 2006/0060842 A1 * | 3/2006 | Sano et al. | ...................... | 257/40 |
| 2006/0204787 A1 * | 9/2006 | Sano et al. | ...................... | 428/690 |
| 2006/0263635 A1 * | 11/2006 | Ise | .................. | 428/690 |
| 2007/0190359 A1 | 8/2007 | Knowles et al. | | |
| 2008/0297033 A1 | 12/2008 | Knowles et al. | | |
| 2009/0153045 A1 * | 6/2009 | Kinoshita et al. | ............. | 313/504 |
| 2009/0218938 A1 * | 9/2009 | Takeda et al. | ................. | 313/504 |
| 2011/0049496 A1 * | 3/2011 | Fukuzaki | ........................ | 257/40 |

FOREIGN PATENT DOCUMENTS

JP 2007-096255 A 4/2007

OTHER PUBLICATIONS

J.A. Gareth Williams, Optimising the luminescence of platinum (II) complexes and their application in organic light emitting devices, 2008, Coordination Chemistry Reviews 252, 2596-2611.*
J.A. Gareth Williams, Photochemistry and Photophysics of Coordination Compounds:Platinum, 2007, Springer-Verlag Berlin Heidelberg, Top Curr Chem 281:205-268.*

* cited by examiner

*Primary Examiner* — Kimberly Nguyen
*Assistant Examiner* — Caleb Henry
(74) *Attorney, Agent, or Firm* — Sughrue Mion, PLLC

(57) ABSTRACT

A material for a light emitting device containing a compound represented by the following formula (1):

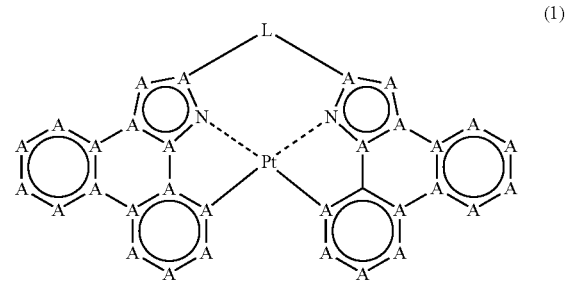

wherein each A independently represents a nitrogen atom or a carbon atom, which may have a substituent, and each of the rings consisting of A and nitrogen atoms independently represents an aromatic ring or an aromatic heterocyclic ring; and L represents a divalent linking group.

14 Claims, 1 Drawing Sheet

ORGANIC ELECTROLUMINESCENCE DEVICE

CROSS-REFERENCE TO RELATED APPLICATION(S)

The present application claims priority from Japanese Patent Application Nos. 2009-228685 filed on Sep. 30, 2009, and 2010-017478 filed on Jan. 28, 2010, the entire content of which is incorporated herein by reference.

BACKGROUND

1. Field

The present invention relates to a material for organic electroluminescence device (also referred to as "an organic EL device material"), an organic electroluminescence device (also referred to as "an organic EL device"), a manufacturing method of a compound used therein, and a light emitting apparatus and an illuminating apparatus using the same device.

2. Description of the Related Art

Since organic electroluminescence devices are capable of obtaining high luminance light emission by low voltage driving, they are actively researched and developed in recent years. An organic electroluminescence device generally has a pair of electrodes and at least one organic layer including a light emitting layer between the pair of electrodes, and electrons injected from the cathode and holes injected from the anode are recombined in the organic layer, and generated energy of exciton is used for emission of light.

Increment in efficiency of devices has been advanced by the use of phosphorescent materials. Iridium complexes and platinum complexes are known as the phosphorescent materials, and a platinum complex light emitting material capable of light emission of blue to green is reported. There is disclosed in US 2008-0297033 a complex of a ligand having a condensed ring structure and iridium or platinum. A platinum complex using a tetradentate ligand having a symmetrical structure of allylazole is disclosed in JP-A-2007-096255. The light emitting layer of an organic electroluminescence device using emission of phosphorescence is formed by the addition of a phosphorescent material to a material transporting charge (a host material).

A phosphorescent material theoretically necessitates wider energy gap than a fluorescent material. In particular, in a blue region going through a light emitting process from a high energy state, since great electric load is applied to the phosphorescent material, development of a blue phosphorescent material capable of achieving high efficiency and high durability in a pure blue region of short wavelength has been difficult. There has been reported recently in US 2008-0297033 that devices using an Ir metal complex having a condensed heterocyclic ring as a bidentate ligand as the phosphorescent material show high durability. However, it is known that the light emitting efficiency of such devices is as low as 4 to 6% to theoretically capable light emitting efficiency of 20% of phosphorescent materials. Although the light emitting efficiency of such devices can be improved by the introduction of a substituent into a specific position, but it is reported that the durability lowers in such devices, so that the compatibility of performances cannot be attained yet. Each of the ligands on Ir is independent from each other and the metal complex has a bulky structure having condensed four rings, so that it is presumed due to the fact that the route of thermal deactivation of energy by structural change is great. Further, the structure of the complex is liable to change by the introduction of a substituent, and the bond length between the ligand and Ir easily changes, which presumably lowers the durability.

In US 2008-0297033 and US 2007-0190359 are also reported the methods of synthesizing alkylphenanthridine which is a useful intermediate for the synthesis of a metal complex compound. However, it has been clearly shown by the examinations of the present inventors that the efficiency of reaction from compound 1 to compound 2 in the following reaction scheme is bad and the yield of compound 2 is low.

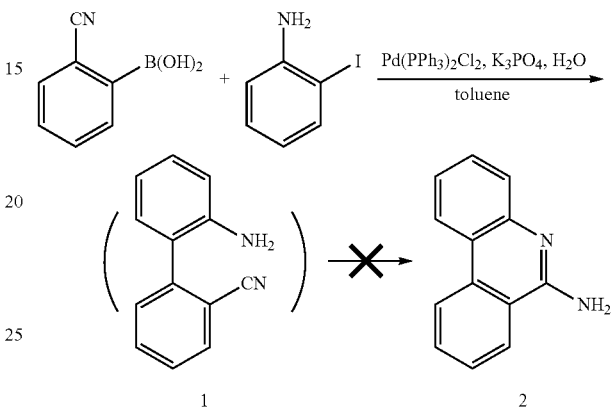

SUMMARY

When light emitting efficiency of an organic EL device lowers, necessary voltage per light emitting quantity becomes large and consumptive power increases. This problem has not yet been dissolved even when the organic EL devices described, e.g., in US 2008-0297033 and JP-A-2007-096255 are used. Although the metal complex disclosed in US 2008-0297033 is a blue light emitting material of good chromaticity, it is reported that the maintenance of high efficiency is difficult and the effect of light emission cannot be obtained according to the kind of substituent of the ligand, and further, the durability of device lowers with the material improved in efficiency. Further, as to the metal complex described in JP-A-2007-096255, descriptions are not found concerning the efficiency.

An object of the invention is to provide a material for a light emitting device capable of manufacturing an organic electroluminescence device having excellent light emitting characteristics, and excellent in light emitting efficiency and durability. Another object is to provide an organic electroluminescence device having excellent light emitting characteristics, and excellent in light emitting efficiency and durability.

The invention has been achieved by finding that light emitting efficiency of the device can be greatly improved by making the structural change small with rigid conformation while maintaining high durability with a condensed ring azole ligand as the platinum tetradentate ligand, and by fixing conformation. This effect is effective in particular in a material having a large energy gap. Specifically, the invention exhibits great effect particularly to a blue light emitting device.

The present inventors have achieved the above objects by the invention having the following constitutions.

[1] A material for a light emitting device containing a compound represented by the following formula (1).

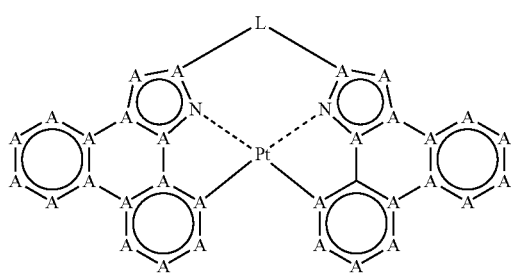

(1)

In formula (1), each A independently represents a nitrogen atom or a carbon atom, which may have a substituent, and each of the rings consisting of A and nitrogen atoms independently represents an aromatic ring or an aromatic heterocyclic ring; and L represents a divalent linking group.

[2] The material for a light emitting device as described in [1], wherein the compound represented by formula (1) is a compound represented by the following formula (2).

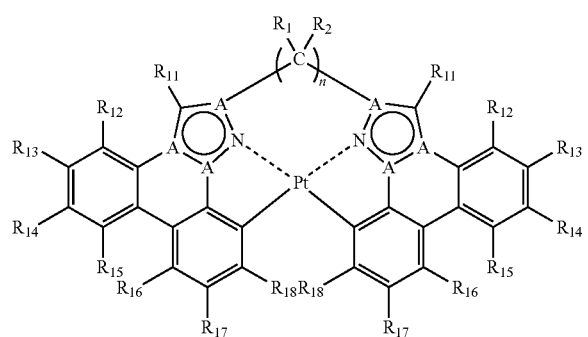

(2)

In formula (2), each of $R_1$ and $R_2$ independently represents a hydrogen atom or a hydrocarbon group, and they may be linked to each other to form a ring; each A independently represents a nitrogen atom or a carbon atom, a ring consisting of A, carbon atoms and nitrogen atoms represents an aromatic heterocyclic ring; n represents an integer of 1 or 2; and each of $R_{11}$ to $R_{18}$ independently represents a hydrogen atom or a substituent.

[3] The material for a light emitting device as described in [2], wherein the compound represented by formula (2) is a compound represented by the following formula (3).

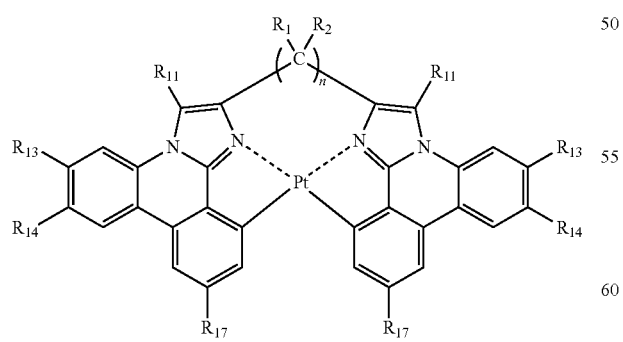

(3)

In formula (3), each of $R_1$ and $R_2$ independently represents a hydrogen atom or a hydrocarbon group; n represents an integer of 1 or 2; and each of $R_{11}$, $R_{13}$, $R_{14}$ and $R_{17}$ independently represents a hydrogen atom or a substituent.

[4] The material for a light emitting device as described in [2], wherein the compound represented by formula (2) is a compound represented by the following formula (4).

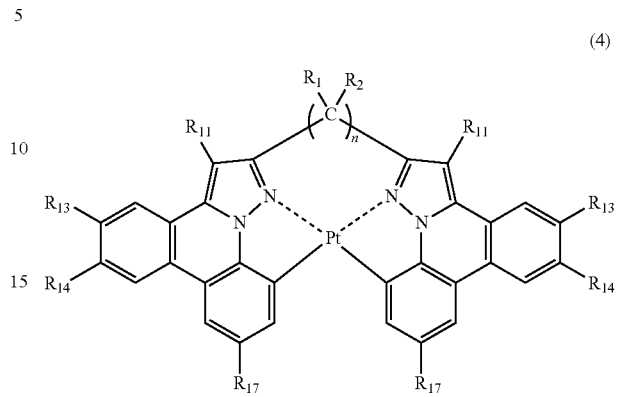

(4)

In formula (4), each of $R_1$ and $R_2$ independently represents a hydrogen atom or a hydrocarbon group; n represents an integer of 1 or 2; and each of $R_{11}$, $R_{13}$, $R_{14}$ and $R_{17}$ independently represents a hydrogen atom or a substituent.

[5] The material for a light emitting device as described in [2], wherein at least one of $R_{12}$ to $R_{18}$ in formula (2) represents a hydrocarbon group having 1 to 10 carbon atoms.

[6] An organic electroluminescence device having a pair of electrodes and an organic layer including a light emitting layer between the pair of electrodes, wherein the organic layer contains the compound represented by any of formulae (1) to (4) described in [1].

[7] The organic electroluminescence device as described in [6], wherein the layer containing the compound represented by formula (1) is the light emitting layer.

[8] The organic electroluminescence device as described in [6], wherein the light emitting layer further contains a hydrocarbon compound.

[9] The organic electroluminescence device as described in [8], wherein the hydrocarbon compound is a compound represented by the following formula (VI).

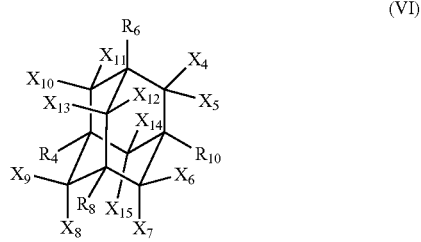

(VI)

In formula (VI), each of $R_4$, $R_6$, $R_8$, $R_{10}$, $X_4$ to $X_{15}$ independently represents a hydrogen atom or a substituent.

[10] The organic electroluminescence device as described in [6], wherein the electrodes include an anode, a charge transporting layer is present between the light emitting layer and the anode, and the charge transporting layer contains a carbazole compound.

[11] The organic electroluminescence device as described in [10], wherein the carbazole compound is a carbazole compound represented by the following formula (a).

(a)

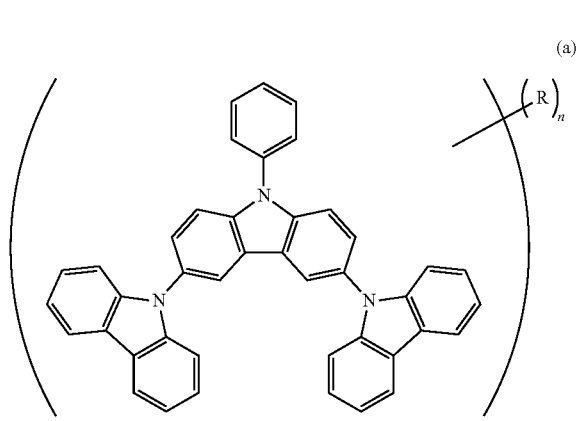

In formula (a), R represents a substituent capable of substituting on the hydrogen atom of the compound; when there are two or more R's, each R may be the same with or different from every other R; and n represents an integer of 0 to 8.

[12] The organic electroluminescence device as described in [10], wherein the carbazole compound is a carbazole compound represented by the following formula (b).

(b)

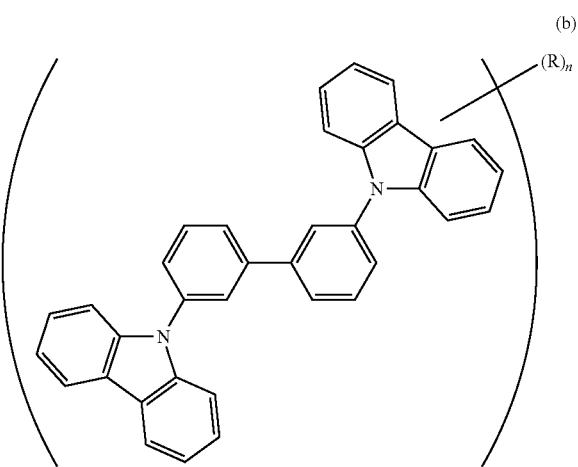

In formula (b), R represents a substituent capable of substituting on the hydrogen atom of the compound; when there are two or more R's, each R may be the same with or different from every other R; and n represents an integer of 0 to 8.

[13] A display using the organic electroluminescence device as described in [6].

[14] An illuminating apparatus using the organic electroluminescence device as described in [6].

According to the invention, a material for a light emitting device capable of manufacturing an organic electroluminescence device excellent in light emitting characteristics, light emitting efficiency and durability can be provided, and an organic electroluminescence device excellent in light emitting characteristics, light emitting efficiency and durability can also be provided. The invention can further provide a displaying apparatus and an illuminating apparatus using the organic electroluminescence device.

BRIEF DESCRIPTION OF DRAWINGS

A general configuration that implements the various features of the invention will be described with reference to the drawings. The drawings and the associated descriptions are provided to illustrate embodiments of the invention and not to limit the scope of the invention.

DETAILED DESCRIPTION OF EXEMPLARY EMBODIMENTS

Figure 1:
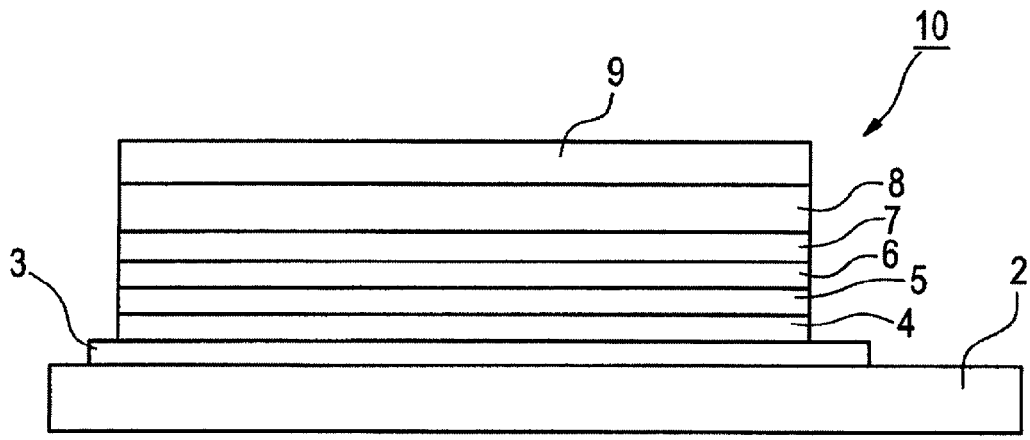
FIG. 1 is a schematic view showing an example of layer constitution of the organic EL device according to the invention (a first embodiment).

Substituent group B is defined as follows in the specification of the invention.

Substituent Group B:

An alkyl group (preferably having a carbon number of 1 to 30, more preferably from 1 to 20, still more preferably from 1 to 10, e.g., methyl, ethyl, isopropyl, tert-butyl, n-octyl, n-decyl, n-hexadecyl, cyclopropyl, cyclopentyl, cyclohexyl), an alkenyl group (preferably having a carbon number of 2 to 30, more preferably from 2 to 20, still more preferably from 2 to 10, e.g., vinyl, allyl, 2-butenyl, 3-pentenyl), an alkynyl group (preferably having a carbon number of 2 to 30, more preferably from 2 to 20, still more preferably from 2 to 10, e.g., propargyl, 3-pentynyl), an aryl group (preferably having a carbon number of 6 to 30, more preferably from 6 to 20, still more preferably from 6 to 12, e.g., phenyl, p-methylphenyl, naphthyl, anthranyl), an amino group (preferably having a carbon number of 0 to 30, more preferably from 0 to 20, still more preferably from 0 to 10, e.g., amino, methylamino, dimethylamino, diethylamino, dibenzylamino, diphenylamino, ditolylamino), an alkoxy group (preferably having a carbon number of 1 to 30, more preferably from 1 to 20, still more preferably from 1 to 10, e.g., methoxy, ethoxy, butoxy, 2-ethylhexyloxy), an aryloxy group (preferably having a carbon number of 6 to 30, more preferably from 6 to 20, still more preferably from 6 to 12, e.g., phenyloxy, 1-naphthyloxy, 2-naphthyloxy), a heterocyclic oxy group (preferably having a carbon number of 1 to 30, more preferably from 1 to 20, still more preferably from 1 to 12, e.g., pyridyloxy, pyrazyloxy, pyrimidyloxy, quinolyloxy), an acyl group (preferably having a carbon number of 1 to 30, more preferably from 1 to 20, still more preferably from 1 to 12, e.g., acetyl, benzoyl, formyl, pivaloyl), an alkoxycarbonyl group (preferably having a carbon number of 2 to 30, more preferably from 2 to 20, still more preferably from 2 to 12, e.g., methoxycarbonyl, ethoxycarbonyl), an aryloxycarbonyl group (preferably having a carbon number of 7 to 30, more preferably from 7 to 20, still more preferably from 7 to 12, e.g., phenyloxycarbonyl), an acyloxy group (preferably having a carbon number of 2 to 30, more preferably from 2 to 20, still more preferably from 2 to 10, e.g., acetoxy, benzoyloxy), an acylamino group (preferably having a carbon number of 2 to 30, more preferably from 2 to 20, still more preferably from 2 to 10, e.g., acetylamino, benzoylamino), an alkoxycarbonylamino group (preferably having a carbon number of 2 to 30, more preferably from 2 to 20, still more preferably from 2 to 12, e.g., methoxycarbonylamino), an aryloxycarbonylamino group (preferably having a carbon number of 7 to 30, more preferably from 7 to 20, still more preferably from 7 to 12, e.g., phenyloxycarbonylamino), a sulfonylamino group (preferably having a carbon number of 1 to 30, more preferably from 1 to 20, still more preferably from 1 to 12, e.g., methanesulfonylamino, benzenesulfonylamino), a sulfamoyl group (preferably having a carbon number of 0 to 30, more preferably from 0 to 20, still more preferably from 0 to 12, e.g., sulfamoyl, methylsulfamoyl, dimethylsulfamoyl, phenylsulfamoyl), a carbamoyl group (preferably having a carbon number of 1 to 30, more preferably from 1 to 20, still more preferably from 1 to 12, e.g., carbamoyl, methylcarbamoyl, diethylcarbamoyl, phenylcarbamoyl), an alkylthio group (preferably having a carbon number of 1 to 30, more preferably from 1 to 20, still more preferably from 1 to 12, e.g., methylthio, ethylthio), an arylthio group (preferably having a carbon number of 6 to 30, more preferably from 6 to 20, still more preferably from 6 to 12, e.g., phenylthio), a heterocyclic thio group (preferably having a carbon number of 1 to 30, more preferably from 1 to 20, still more preferably from 1 to 12, e.g., pyridylthio, 2-benzimizolylthio, 2-benzoxazolylthio, 2-benzothiazolylthio), a sulfonyl group (preferably having a carbon number of 1 to 30, more preferably from 1 to 20, still more preferably from 1 to 12, e.g., mesyl, tosyl), a sulfinyl group (preferably having a carbon number of 1 to 30, more preferably from 1 to 20, still more preferably from 1 to 12, e.g., methanesulfinyl, benzenesulfinyl), an ureido group (preferably having a carbon number of 1 to 30, more preferably from 1 to 20, still more preferably from 1 to 12, e.g., ureido, methylureido, phenylureido), a phosphoric acid amido group (preferably having a carbon number of 1 to 30, more preferably from 1 to 20, still more preferably from 1 to 12, e.g., diethylphosphoric acid amido, phenylphosphoric acid amido), a hydroxy group, a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic (heteroaryl) group (preferably having a carbon number of 1 to 30, more preferably from 1 to 12; examples of the heteroatom include a nitrogen atom, an oxygen atom and a sulfur atom; specifically an imidazolyl group, a pyridyl group, a quinolyl group, a furyl group, a thienyl group, a piperidyl group, a morpholino group, a benzoxazolyl group, a benzimidazolyl group, a benzothiazolyl group, a carbazolyl group, an azepinyl group and the like), a silyl group (preferably having a carbon number of 3 to 40, more preferably from 3 to 30, still more preferably from 3 to 24, e.g., trimethylsilyl, triphenylsilyl), and a silyloxy group (preferably having a carbon number of 3 to 40, more preferably from 3 to 30, still more preferably from 3 to 24, e.g., trimethylsilyloxy, triphenylsilyloxy), a phosphoryl group (e.g., diphenylphosphoryl group, dimethylphosphoryl group). These substituents may be further substituted, with a substituent selected from the above-exemplified substituent group B.

The hydrogen atoms in the explanation of formulae (1) to (4) also include isotopes (deuterium atoms and the like), and the atoms further constituting substituents also include the isotopes thereof.

The material for a light emitting device in the invention contains a compound represented by formula (1).

Further, the organic electroluminescence device in the invention is an organic electroluminescence device having a light emitting layer between a pair of electrodes, and having a layer containing a compound represented by formula (1).

In the invention, by the use of a platinum complex having a rigid tetradentate ligand, any compound represented by formula (1) can manufacture a highly efficient and highly durable organic electroluminescence device without depending upon a substituent.

Further, the outside condensed ring of the compound represented by formula (1) is a 6-membered ring. According to this structure, coordination of a plane quadrangle can be still more stabilized in a platinum tetradentate ligand and thermal stability can be greatly improved.

Platinum complexes generally have Ea greater than that of Ir and a barrier to injection of electrons into light emitting layers is low. Accordingly, there are cases where electrons pass through without being trapped by light emitting layers to hinder generation of exciton in light emitting layers. At this time, by the use jointly with a charge transporting layer using a material small in Ea containing a carbazole compound on the anode side, efficiency can be preferably improved.

The compound represented by formula (1) is described below.

Compound Represented by Formula (1):

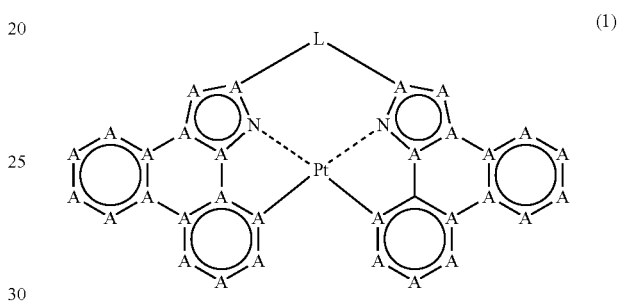

In formula (1), each A independently represents a nitrogen atom or a carbon atom, which may have a substituent, and each of the rings consisting of A and nitrogen atoms independently represents an aromatic ring or an aromatic heterocyclic ring. Each of the rings consisting of A and nitrogen atoms represents an aromatic ring or an aromatic heterocyclic ring. L represents a divalent linking group.

Each A independently represents a nitrogen atom or a carbon atom and may have a substituent. From the viewpoint of chemical stability, the number of nitrogen atoms in formula (1) is preferably 2 to 8, more preferably 4 to 6, and still more preferably 4.

Substituent group B is exemplified as the substituents in the case where A has a substituent. Adjacent substituents may be bonded to each other to form a ring. The examples of the substituents preferably include a hydrogen atom, a halogen atom (e.g., a fluorine atom, a chlorine atom, an iodine atom and a bromine atom), and a saturated or unsaturated hydrocarbon group having 1 to 10 carbon atoms, more preferably a hydrogen atom, a fluorine atom, an alkyl group having 1 to 10 carbon atoms, or an aryl group having 6 to 10 carbon atoms, and especially preferably a hydrogen atom and an alkyl group having 3 to 6 carbon atoms. The substituent of A may further have a substituent. The further substituents are the same with the examples of the substituents of A, and preferred substituents are also the same.

It has been found that when the substituent of A is a hydrocarbon group having 1 to 10 carbon atoms, occurrence of color purity aberration by long wavelength light emission caused by the addition of the compound represented by formula (1) in high concentration can be prevented. Since the planarity of the ligand of the compound represented by formula (1) is high, the long wavelength light emission is resulted from the formation of excimer or excimers by the interaction of platinum-platinum in a membrane added in high concentration. It is thought that by the introduction of a hydrocarbon substituent having an appropriate size, approaching of mutual platinum planes is prevented. While when the carbon atom number is greater than 10, the polarity of the molecule becomes extremely small and the compatibility with the host molecule is lowered, as a result long wavelength light emission by agglomeration of metal complex molecules is to be observed again.

In formula (1), from the viewpoint of chemical stability, the 5-membered ring part consisting of A and nitrogen atoms is preferably a pyrrole ring, an imidazole ring, a pyrazole ring or a triazole ring. Further, as the energy gap of the ligand is wide and the light emitting wavelength of the complex can be shortened, an imidazole ring, a pyrazole ring or a triazole ring is more preferred. From the point that bonding energy of the heterocyclic ring and the platinum is high and the device to be obtained is excellent in durability, an imidazole ring is most preferred.

L represents a divalent linking group. It is easy for a platinum tetradentate complex to take a planar structure, since all the bonding hands from the platinum are on the same plane. It is known, accordingly, that the excimer of a complex is often formed by the interaction of π orbit of the ligand, dipole moment, and $d_z$ orbit of the platinum. The excimer is narrow in energy gap and results in deteriorations of sharpness of light emission spectrum and light emitting efficiency. Since the polar moment of the entire molecule lowers by using a low polarity linking group in L, light emission by association due to agglomeration of the complex can be controlled and color purity can be improved.

The divalent linking group represented by L is preferably low polarity, and the examples of the divalent linking groups include an alkylene group (methylene, ethylene, propylene and the like), an arylene group (phenylene, naphthalenediyl), a heteroarylene group (pyridinediyl, thiophenediyl and the like), an imino group (—NR'—) (phenylimino and the like), an oxy group (—O—), a thio group (—S—), a phosphinidene group (—PR'—) (phenylphosphinidene and the like), a silylene group (—SiRR'—) (dimethylsilylene, diphenylsilylene and the like), and combinations of these groups (wherein each of R and R' independently represents a substituent, and substituent group B is exemplified as the examples of the substituents). These linking groups may further have a substituent. Substituent group B is exemplified as the examples of further substituents, and an alkyl group having 1 to 10 carbon atoms is preferred.

The following linking groups are preferably exemplified as L.

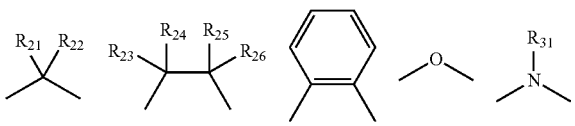

Each of $R_{23}$ to $R_{26}$ and $R_{31}$ independently represents a hydrogen atom or a divalent substituent. Each of $R_{21}$ and $R_{22}$ independently represents a hydrogen atom, an alkyl group or an aryl group.

Each of $R_{23}$ to $R_{26}$ and $R_{31}$ independently represents a hydrogen atom or a divalent substituent.

Each of $R_{23}$ to $R_{26}$ preferably represents a hydrogen atom, an aromatic heterocyclic group, an alkyl group having 1 to 10 carbon atoms, or an aryl group having 6 to 10 carbon atoms, more preferably represents a hydrogen atom, an alkyl group having 1 to 10 carbon atoms, or an aryl group having 6 to 10 carbon atoms, and still more preferably a hydrogen atom or an alkyl group having 1 to 6 carbon atoms.

$R_{31}$ preferably represents a hydrogen atom, an aromatic heterocyclic group, or a saturated or unsaturated hydrocarbon group having 20 or less carbon atoms, more preferably represents a hydrogen atom, an alkyl group having 1 to 6 carbon atoms, or an aryl group, still more preferably a hydrogen atom, a methyl group, a phenyl group, or an ethyl group, and especially preferably a methyl group.

Each of $R_{21}$ and $R_{22}$ independently represents a hydrogen atom, an aryl group, or an alkyl group, more preferably represents a hydrogen atom, an alkyl group having 1 to 10 carbon atoms, or an aryl group having 6 to 10 carbon atoms, and still more preferably a methyl group or a phenyl group.

Of the above, from the point of durability, L preferably represents an alkylene group, and more preferably a methylene group or an ethylene group.

In the invention, the compound represented by formula (1) is preferably a compound represented by the following formula (2).

(2)

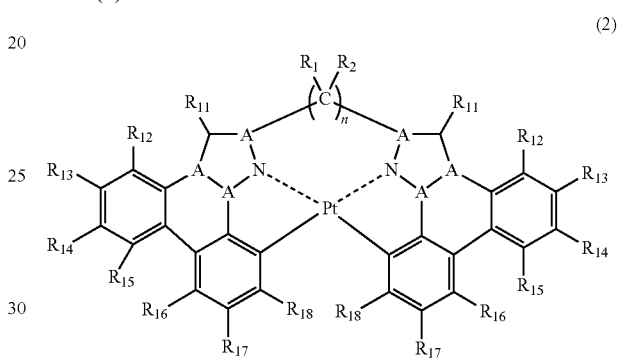

In formula (2), A has the same meaning as the meaning of A in formula (1). The ring consisting of A, carbon atoms and nitrogen atom represents an aromatic heterocyclic ring. Each of $R_1$ and $R_2$ independently represents a hydrogen atom or a hydrocarbon group. n represents an integer of 1 or 2. Each of $R_{11}$ to $R_{18}$ independently represents a hydrogen atom or a substituent. Adjacent substituents may be bonded to each other to form a ring.

A has the same meaning as the meaning of A in formula (1), and preferred examples are also the same.

The ring constituted by A, carbon atoms and nitrogen atoms is the same as the ring constituted by A and nitrogen atoms in formula (1), and preferred examples are also the same.

The hydrocarbon group represented by $R_1$ and $R_2$ may independently have a substituent, and may be saturated or unsaturated. As the groups that may be substituted, substituent group B described above is exemplified, and any group may be used so long as it is substitutable. Each of $R_{23}$ to $R_{26}$ preferably represents a hydrogen atom, an aromatic heterocyclic group, an alkyl group having 1 to 10 carbon atoms, or an aryl group having 6 to 10 carbon atoms, more preferably represents a hydrogen atom, an alkyl group having 1 to 10 carbon atoms, or an aryl group having 6 to 10 carbon atoms, and still more preferably a hydrogen atom or an alkyl group having 1 to 6 carbon atoms. The substituents may further have a substituent. Substituent group B is exemplified as the examples of further substituents, preferably the examples include an aryl group and an alkyl group, more preferably an alkyl group having 1 to 10 carbon atoms, and still more preferably include a methyl group, an ethyl group, an isopropyl group, a t-butyl group, and a neopentyl group.

Each of $R_1$ and $R_2$ independently preferably represents a hydrogen atom, an aryl group, or an alkyl group, more preferably represents a hydrogen atom, an alkyl group having 1 to 10 carbon atoms, or an aryl group having 6 to 10 carbon atoms, and still more preferably a methyl group or a phenyl group.

Each of $R_{11}$ to $R_{18}$ independently represents a hydrogen atom or a substituent. Each substituent may further have a substituent. Substituent group B is exemplified as the examples of further substituents, preferably the examples include an aryl group and an alkyl group, more preferably an alkyl group having 1 to 10 carbon atoms, and still more preferably a methyl group, an ethyl group, an isopropyl group, a t-butyl group, and a neopentyl group.

$R_{11}$ preferably represents a hydrogen atom, a halogen atom (a fluorine atom, a chlorine atom, an iodine atom, or a bromine atom), or a saturated or unsaturated hydrocarbon group having 8 or less carbon atoms, more preferably a hydrogen atom, a fluorine atom, an alkyl group having 1 to 8 carbon atoms, or an aryl group having 6 to 8 carbon atoms, and especially preferably represents a hydrogen atom, a methyl group, or an aryl group having 6 to 8 carbon atoms.

Each of $R_{12}$ to $R_{18}$ preferably represents a hydrogen atom, a halogen atom (a fluorine atom, a chlorine atom, an iodine atom, or a bromine atom), or a saturated or unsaturated hydrocarbon group having 8 or less carbon atoms, more preferably a hydrogen atom, a halogen atom (a fluorine atom, a chlorine atom, an iodine atom, or a bromine atom), or a saturated or unsaturated hydrocarbon group having 1 to 6 carbon atoms, still more preferably a hydrogen atom, a fluorine atom, an alkyl group having 1 to 10 carbon atoms, or an aryl group having 6 to 10 carbon atoms, and especially preferably represents a hydrogen atom or an alkyl group having 3 to 6 carbon atoms. In $R_{11}$ to $R_{18}$, adjacent substituents may be bonded to each other to form a ring.

Which one of $R_{11}$ to $R_{18}$ may represent a substituent with no particular limitation, but it is preferred that at least one of $R_{12}$ to $R_{18}$ represents a hydrocarbon group having 1 to 10 carbon atoms, and in view of durability, it is preferred that at least any one of $R_{11}$, $R_{13}$, $R_{14}$ and $R_{17}$ represents a substituent, more preferably at least one of $R_{11}$ and $R_{14}$ represents a substituent, and especially preferably $R_{14}$ represents a substituent. This is presumably because $R_{14}$ holds the para-position to the nitrogen-containing 5-membered ring and is susceptible to electric oxidation as compared with other portions.

n represents an integer of 1 to 3, preferably 1 or 2, and more preferably 2.

In the present invention, the compound represented by formula (1) is preferably a compound represented by the following formula (3).

(3)

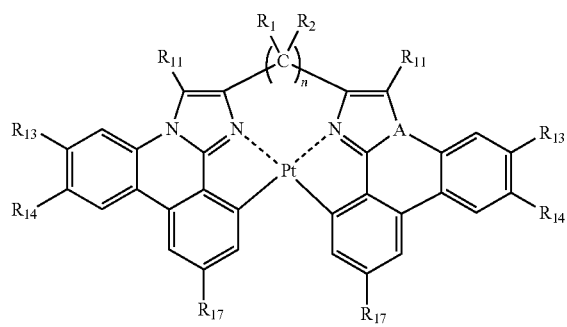

In formula (3), each of $R_1$ and $R_2$ independently represents a hydrogen atom or a hydrocarbon group. n represents an integer of 1 to 3. Each of $R_{11}$, $R_{13}$, $R_{14}$ and $R_{17}$ independently represents a hydrogen atom or a substituent.

$R_1$, $R_2$, $R_{11}$, $R_{13}$, $R_{14}$, $R_{17}$ and n have the same meaning as A, $R_1$, $R_2$, $R_{11}$, $R_{13}$, $R_{14}$, $R_{17}$ and n in formula (1), and preferred examples are also the same.

At least any one of $R_{11}$, $R_{13}$, $R_{14}$ and $R_{17}$ preferably represents a substituent, more preferably $R_{11}$ or $R_{14}$ represents a substituent, and still more preferably $R_{14}$ represents a substituent.

In formula (3), it is preferred that n represents 1 or 2, each of $R_1$ and $R_2$ represents a hydrogen atom or an alkyl group having 1 to 6 carbon atoms, and at least any one of $R_{11}$, $R_{13}$, $R_{14}$ and $R_{17}$ represents a saturated or unsaturated hydrocarbon group having 1 to 10 carbon atoms, it is more preferred that n represents 2, each of $R_1$ and $R_2$ represents a hydrogen atom or an alkyl group having 1 to 6 carbon atoms, and at least any one of $R_{11}$ and $R_{14}$ represents an alkyl group having 1 to 8 carbon atoms, or an aryl group having 6 to 8 carbon atoms, and it is still more preferred that n represents 2, each of $R_1$ and $R_2$ represents a hydrogen atom, and $R_{14}$ represents an alkyl group having 3 to 6 carbon atoms.

In the invention, the compound represented by formula (1) or (2) is preferably a compound represented by the following formula (4). The compound represented by formula (4) is advantageous in that the peak on the long wave side in light emission spectrum is small and luminescence higher in blue purity can be obtained even with the same light emitting maximum wavelength.

(4)

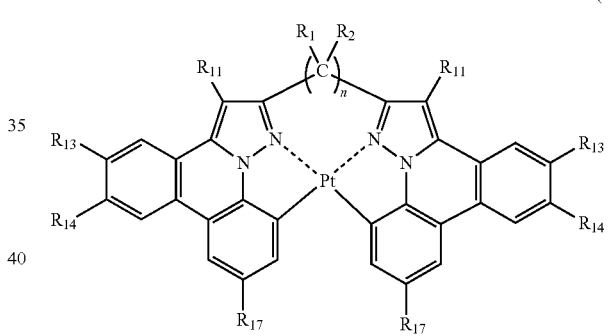

In formula (4), each of $R_1$ and $R_2$ independently represents a hydrogen atom or a hydrocarbon group. n represents an integer of 1 or 2. Each of $R_{11}$, $R_{13}$, $R_{14}$ and $R_{17}$ independently represents a hydrogen atom or a substituent.

$R_1$, $R_2$, $R_{11}$, $R_{13}$, $R_{14}$, $R_{17}$ and n have the same meaning with A, $R_1$, $R_2$, $R_{11}$, $R_{13}$, $R_{14}$, $R_{17}$ and n in formula (1).

At least any one of $R_{11}$, $R_{13}$, $R_{14}$ and $R_{17}$ preferably represents a substituent, more preferably $R_{11}$ or $R_{14}$ represents a substituent, and still more preferably $R_{14}$ represents a substituent.

In formula (4), it is preferred that n is 1 or 2, each of $R_{11}$, $R_{13}$, $R_{14}$ and $R_{17}$ represents a hydrogen atom or an alkyl group having 1 to 6 carbon atoms, and each of $R_1$ and $R_2$ represents an alkyl group having 1 to 6 carbon atoms, and it is more preferred that n is 1, each of $R_1$ and $R_2$ represents an alkyl group having 1 to 6 carbon atoms, and each of $R_{11}$, $R_{13}$, $R_{14}$ and $R_{17}$ represents a hydrogen atom.

The compound represented by formula (1) is advantageous in that light emitting wavelength is short and the effect of the invention is conspicuous in the blue emission region as compared with other compounds.

The function of the compound represented by formula (1) is not restricted, and the layer containing the compound represented by formula (1) is preferably a light emitting layer. When two or more organic layers are present, the compound represented by formula (1) may be contained in any layer besides the layer containing the compound. The compound represented by formula (1) is preferably contained in a light emitting layer, more preferably contained in a light emitting layer as a light emitting material or a host material, still more preferably contained in a light emitting layer as a light emitting material, and especially preferably it is contained in a light emitting layer together with at least a kind of host material.

The specific examples of the compounds represented by any of formulae (1) to (4) are shown below, but the invention is not restricted thereto.

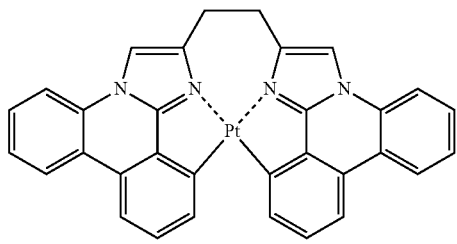

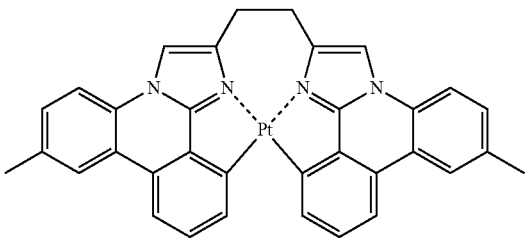

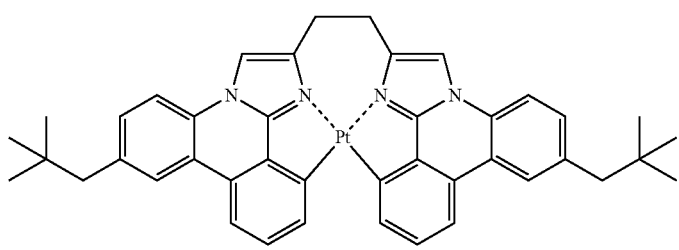

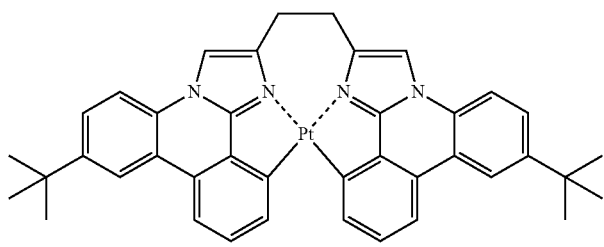

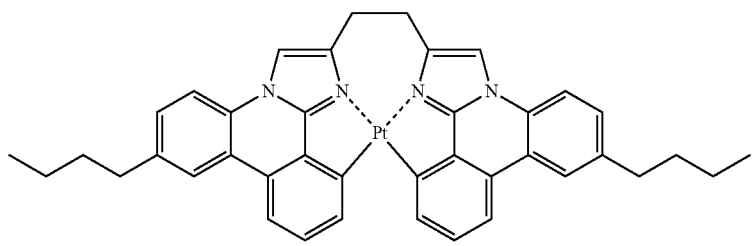

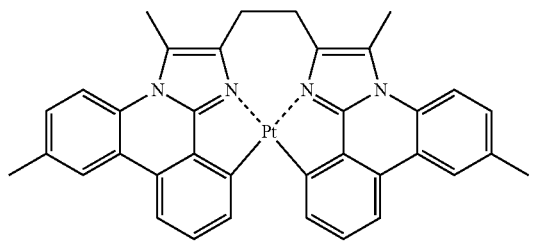

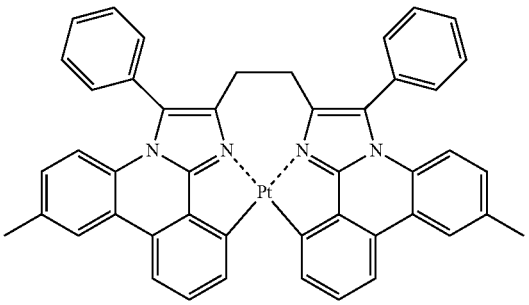

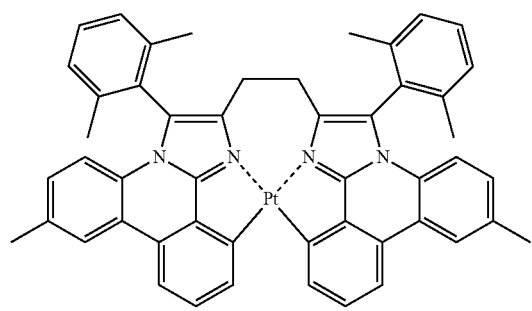
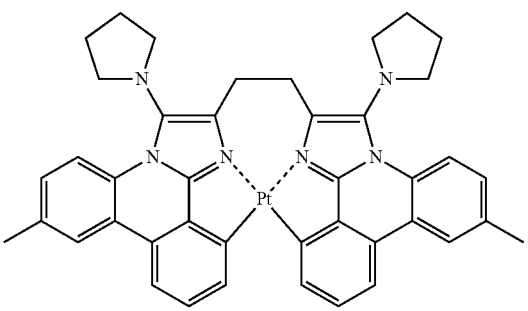
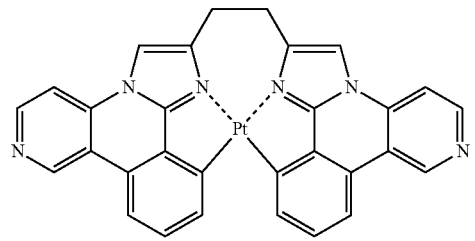
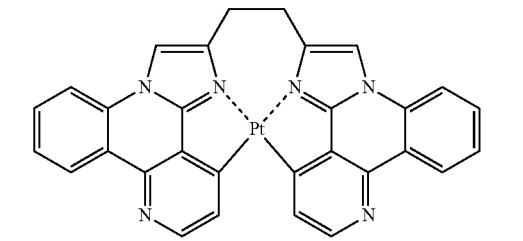
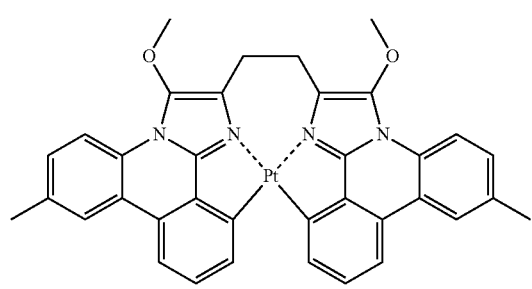
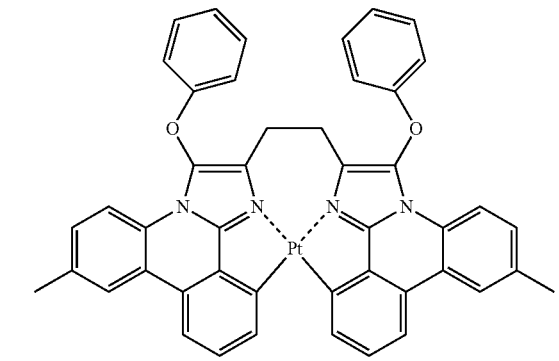
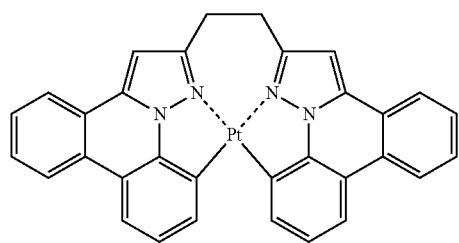
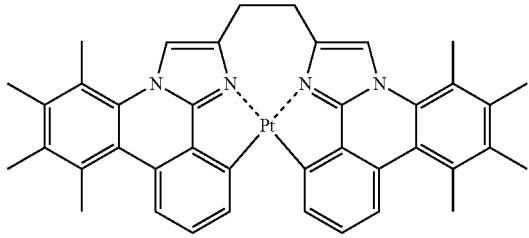
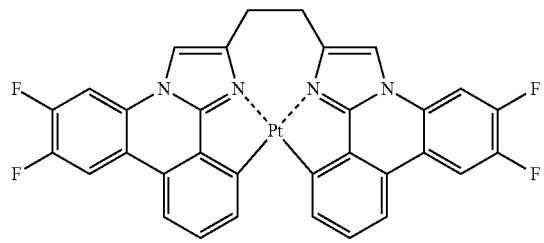
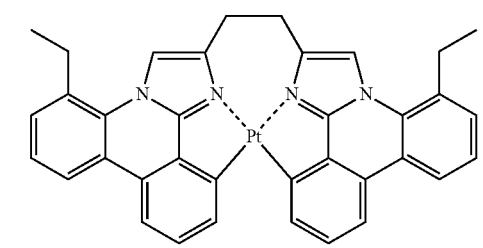
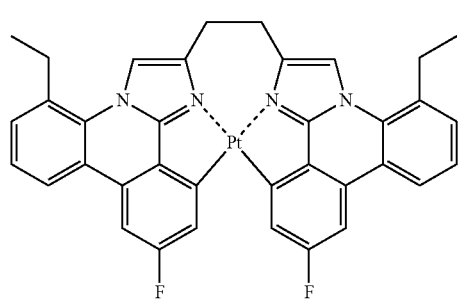
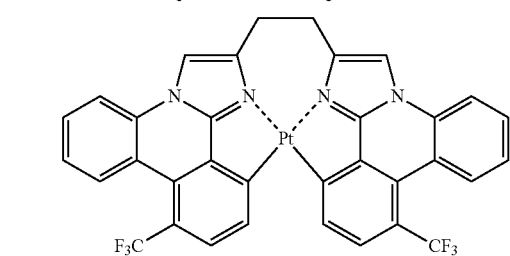

17
18
-continued
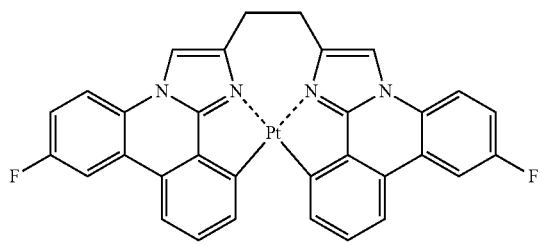
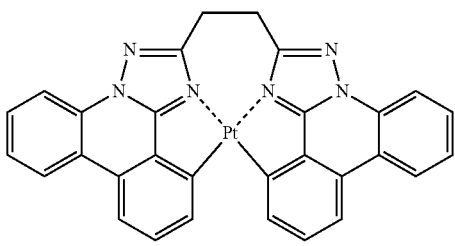
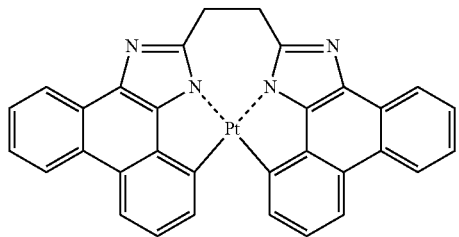
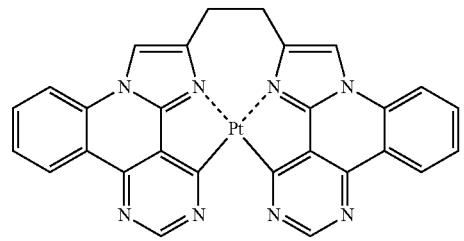
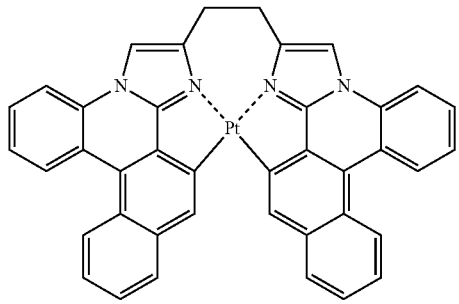
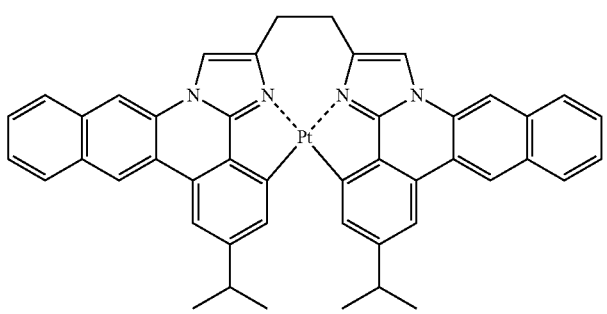
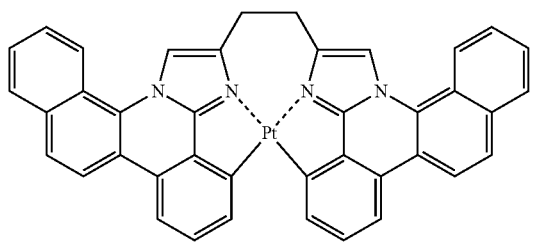
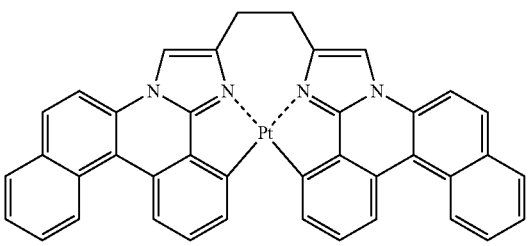
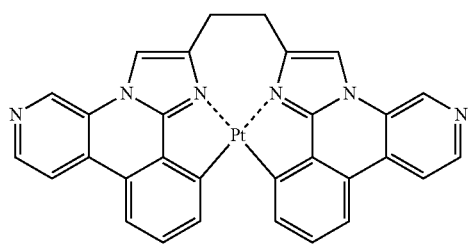
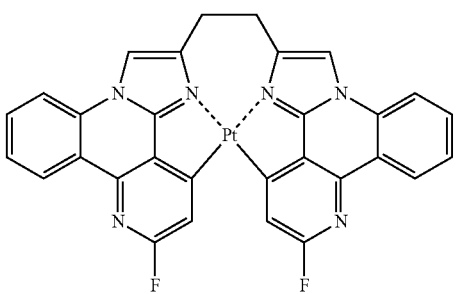
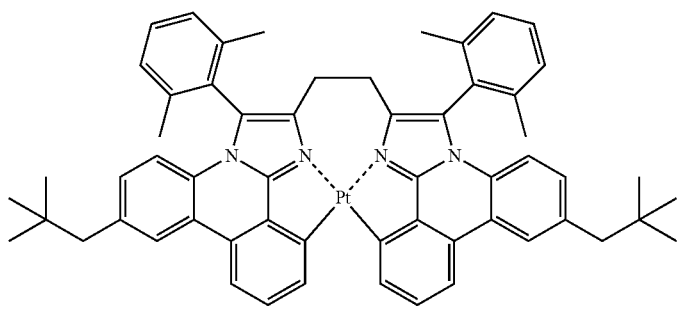

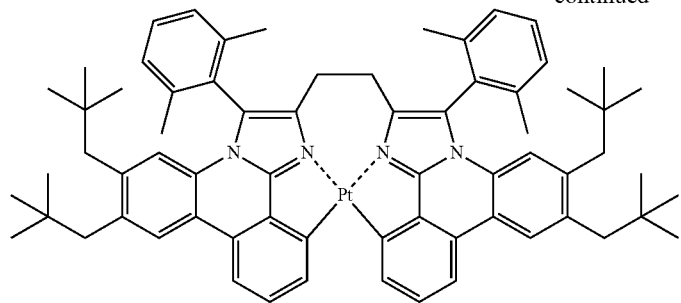
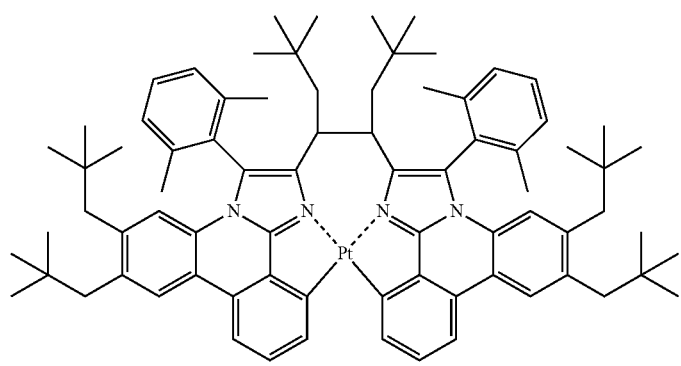
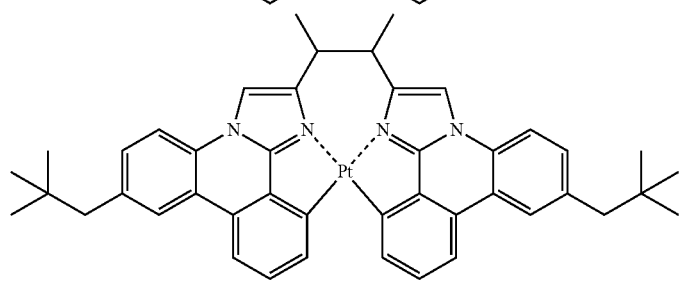
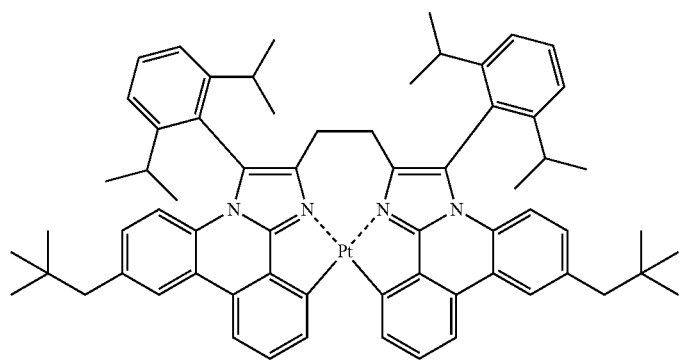
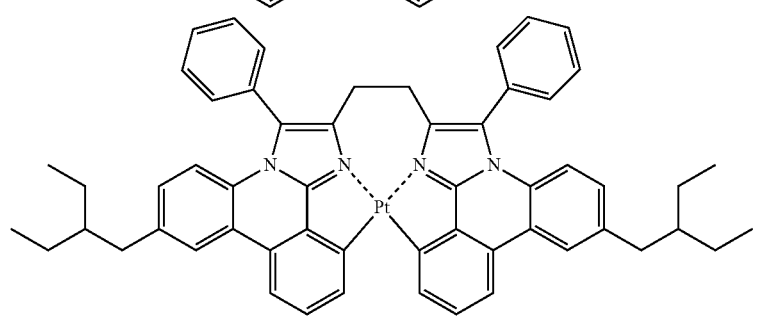

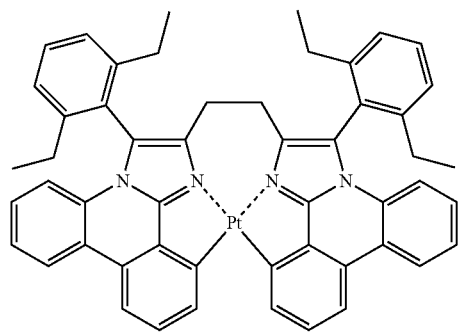
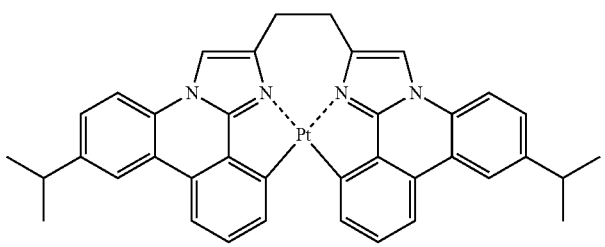
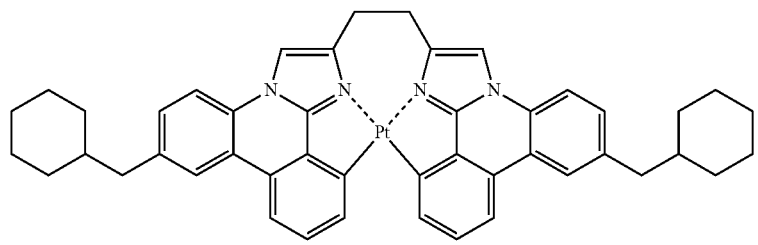
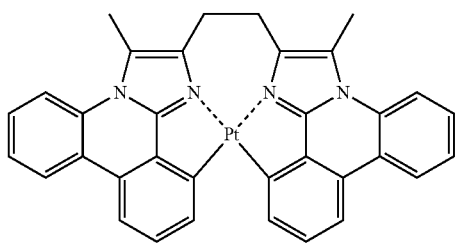
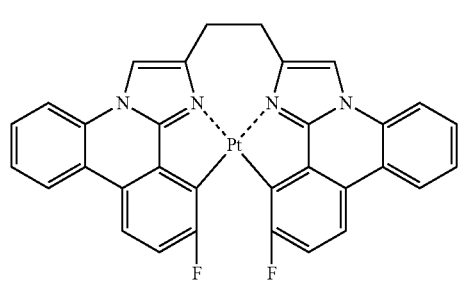
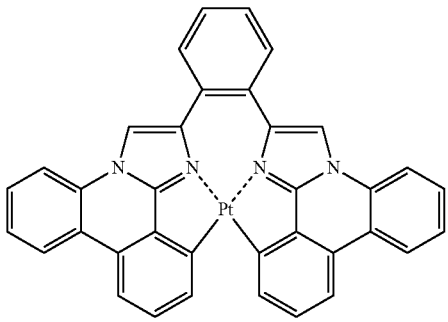
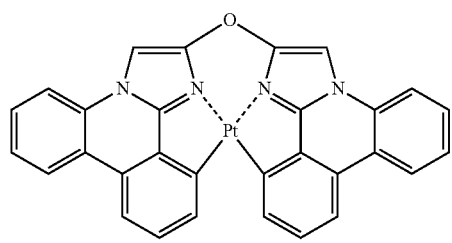
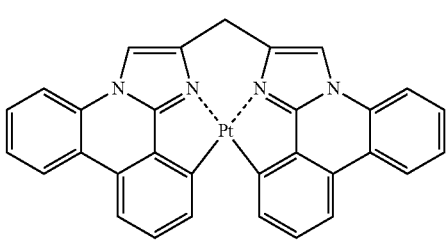
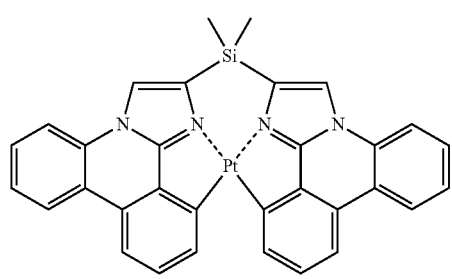
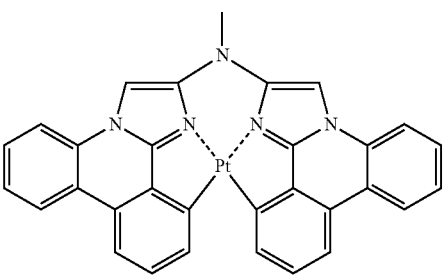

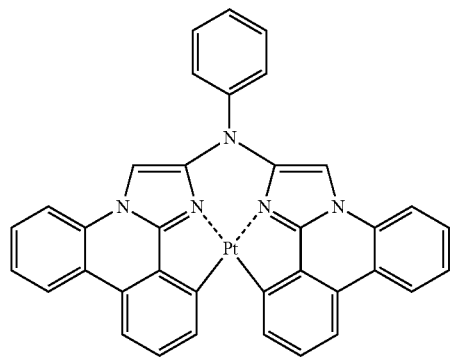
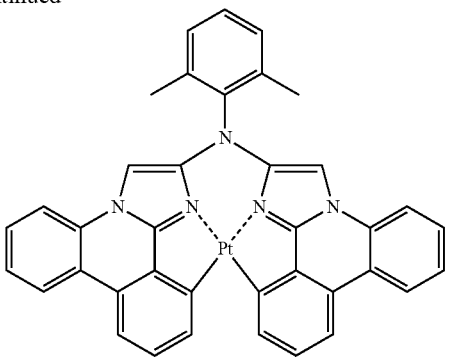
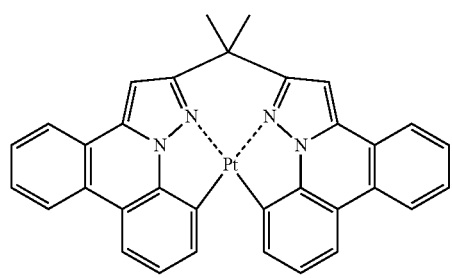
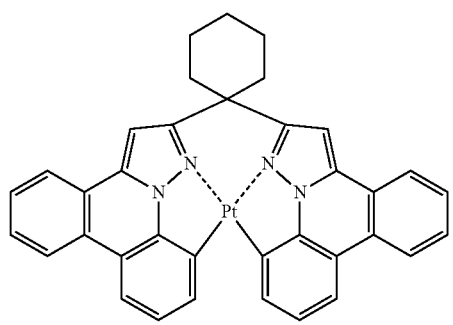
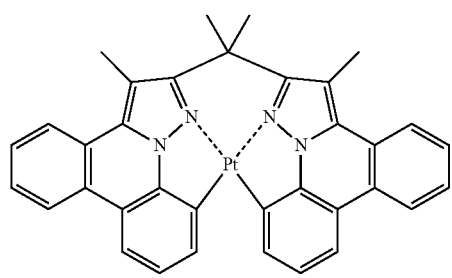
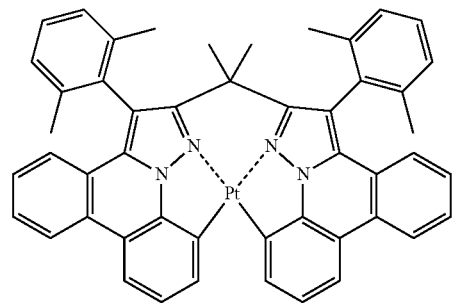
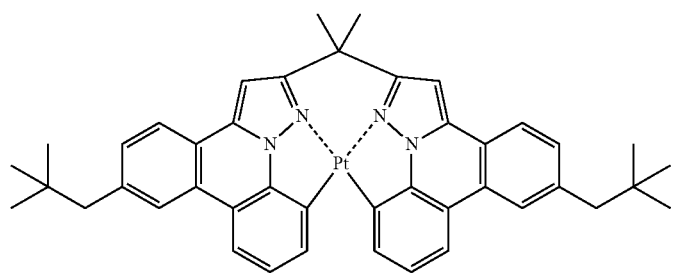

The exemplified compounds as the compounds represented by formula (1) can be synthesized according to, for example, the process shown below.

The above metal complex compounds can be synthesized according to various methods including the methods disclosed in JP-A-2009-161524, paragraphs [0112] to [0122].

Manufacturing Method of a Compound Represented by Formula (10):

The invention also relates to a compound represented by the following formula (10).

The compound represented by formula (10) can be used as the intermediate of the compound represented by formula (1).

The manufacturing method of the compound represented by formula (10) includes the process of reaction of a compound represented by the following formula (a) and a hydrocarbon-metal compound to obtain a compound represented by the following formula (b).

By using the manufacturing method of the invention, the compound represented by formula (10) can be obtained in a high yield as compared with using conventional methods.

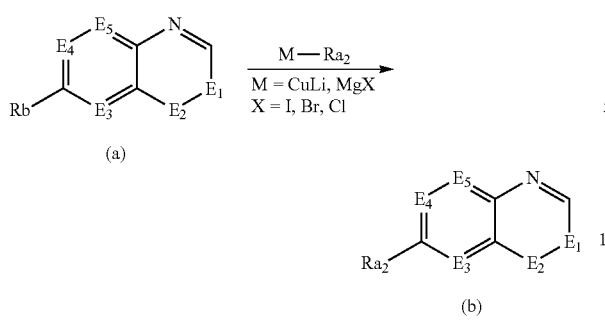

(a)

M = CuLi, MgX
X = I, Br, Cl (b)

In the above formulae, Rb represents a desorption group; $Ra_2$ represents a hydrocarbon substituent; and each of $E_1$ to $E_5$ independently represents a carbon atom or a nitrogen atom which may have a substituent. When $E_1$ and $E_2$, and $E_4$ and $E_5$ respectively have a substituent, these substituents may be bonded to each other to form a ring.

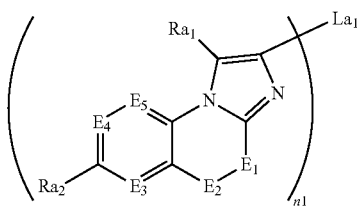

(10)

In formula (10), $Ra_1$ represents a hydrogen atom or a substituent. $Ra_2$ represents a hydrocarbon substituent. Each of $E_1$ to $E_5$ independently represents a carbon atom or a nitrogen atom which may have a substituent. n1 represents an integer of 1 or 2. $La_1$ represents a linking group. When $E_1$ and $E_2$, and $E_4$ and $E_5$ respectively have a substituent, these substituents may be bonded to each other to form a ring, provided that when n1 is 1, $La_1$ represents a hydrogen atom or a monovalent substituent.

Rb represents a desorption group. As the examples of the desorption groups, generally used desorption groups, e.g., an alkylsulfonyloxy group, an arylsulfonyloxy group, a fluorine atom, a chlorine atom, a bromine atom and an iodine atom are exemplified, and a bromine atom is preferred.

As the substituent represented by $Ra_1$, an alkyl group having 6 to 8 carbon atoms, an alkoxy group, and an aryl group can be exemplified. $Ra_1$ preferably represents a hydrogen atom, a methyl group, or an aryl group having 6 to 8 carbon atoms.

The hydrocarbon substituent represented by $Ra_2$ may have a substituent, and may be saturated or unsaturated. As the groups that may be substituted, substituent group B described above is exemplified, and any group may be used so long as it is substitutable. The hydrocarbon substituent represented by $Ra_2$ is preferably an alkyl group having a sum total of 1 to 10 carbon atoms, and more preferably an alkyl group having a sum total of 3 to 8 carbon atoms, e.g., i-propyl, cyclohexyl, t-butyl, n-pentyl, neopentyl, cyclohexylmethyl, benzyl and the like are exemplified.

When n1 is 2, the linking group represented by $La_1$ has the same meaning as L in formula (1), and preferred examples are also the same. When n1 is 1, $La_1$ preferably represents a hydrogen atom or an alkyl group having a sum total of 1 to 10 carbon atom, and more preferably represents a hydrogen atom or a methyl group.

Each of $E_1$ to $E_5$ independently represents a carbon atom or a nitrogen atom having or not having a substituent, and preferably all of $E_1$ to $E_5$ represent a carbon atom. When $E_1$ and $E_2$, and $E_4$ and $E_5$ respectively have a substituent, these substituents may be bonded to each other to form a ring, and preferred is the case where $E_1$ and $E_2$ form a benzene ring with each other, which has a phenanthridine structure. Specifically a structure represented by the following formula (10-1) is exemplified.

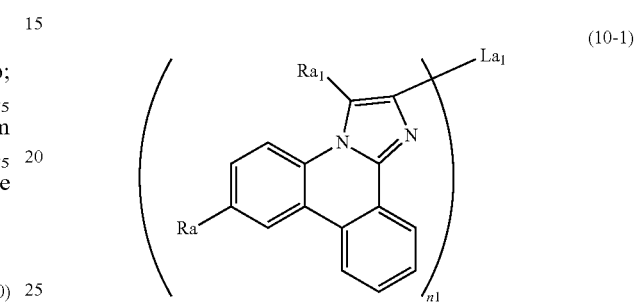

(10-1)

In formula (10-1), $R_{11}$ represents a hydrogen atom or a substituent. Ra represents a hydrocarbon substituent. n1 represents an integer of 1 or 2. $La_1$ represents a linking group, provided that when n1 is 1, $La_1$ represents a hydrogen atom or a monovalent substituent.

A reaction solvent can be used in the process.

An organic acid, an inorganic acid and an organic solvent can be used as preferred reaction solvents, and an organic solvent is especially preferably used. Solvents which do not cause a liquid separation phenomenon at reaction time and capable of providing a solution homogeneous with a solvent are preferred and, for example, alcoholic organic solvents, e.g., methanol, ethanol, propanol, isopropanol, butanol, t-butyl alcohol, amyl alcohol and the like, ketone-based solvents, e.g., acetone, methyl ethyl ketone and the like, diol-based organic solvents, e.g., ethylene glycol, diethylene glycol, triethylene glycol, propylene glycol, dipropylene glycol, 1,3-propanediol and the like, ether-based solvents, e.g., ethylene glycol monomethyl ether, ethylene glycol monoethyl ether, ethylene glycol diethyl ether and the like, and tetrahydrofuran, dioxane, acetonitrile and the like are exemplified. These solvents may be used as mixed solvents of two or more kinds.

The use amount of the solvent is preferably 1 to 250 mass times that of the amount of the compound represented by formula (a), more preferably 5 to 100 mass times, and especially preferably 10 to 50 mass times.

In the invention, the compound represented by formula (a) may be either in a dispersion state in a solvent or in a solution state, but a solution state is preferred.

The use amount of the hydrocarbon-metal compound is preferably 1 to 10 equivalents to the amount of the compound represented by formula (a), more preferably 1.2 to 8 equivalents, and especially preferably 1.5 to 3 equivalents.

The reaction starting temperature is preferably −100 to 10° C., more preferably −80 to 5° C., and still more preferably −60 to 0° C. When the temperature is −80° C. or higher, the reaction is expedited and the time required for the synthesis can be shortened, so that economical. While when the synthesis is carried out at 0° C. or lower, the amount of byproduct can be restrained and the yield is increased, so that preferred.

The compound represented by formula (a) is commercially available.

As the hydrocarbon-metal compounds, a hydrocarbon-lithium compound, a Reformatsky reagent (a halozinc compound), a hydrocarbon-tin compound, a hydrocarbon-cadmium compound, a Gilman reagent (a copper-lithium compound), and a Grignard reagent (a halomagnesium compound) can be exemplified. Of these compounds, a Gilman reagent, a Grignard reagent, and a Reformatsky reagent are preferred, and a Grignard reagent is more preferred.

Above all, when alkyl bromomagnesium and (diphenylphosphino-ferrocenato)dichloronickel, as a reacting agent, are used together, good results can be obtained irrespective of the kind of alkyl group.

Ordinary methods can be used for manufacturing the compound represented by formula (10) from the compound represented by formula (b). For example, various kinds of desired complexes can be synthesized according to the methods disclosed on and after paragraph [0134] in US 2008-0297033 by aminating the compound represented by formula (b) by the methods described in, e.g., *Journal of Chemical Society*, page 2225 (1932), etc.

Preferred of the compounds represented by formula (10) is the case where $E_1$ and $E_2$ form a benzene ring with each other, which has a phenanthridine structure. Specifically a structure represented by the following formula (10-1) is exemplified.

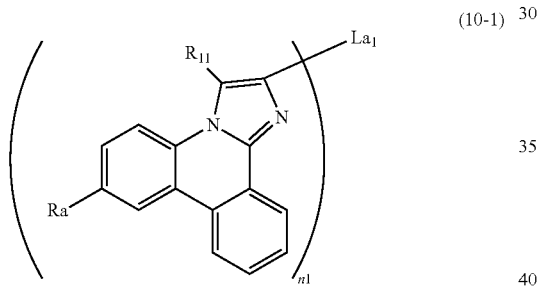

(10-1)

In formula (10-1), $R_{11}$ represents a hydrogen atom or a substituent. Ra represents a hydrocarbon substituent. n1 represents an integer of 1 or 2. $La_1$ represents a linking group, provided that when n1 is 1, $La_1$ represents a hydrogen atom or a monovalent substituent.

The substituent represented by $R_{11}$ is the same with $Ra_1$ in formula (10).

The substituent represented by Ra is the same with $Ra_2$ in formula (10).

As an example of the processes of reaction of a compound represented by formula (a) and a hydrocarbon-metal compound to obtain a compound represented by formula (b), a process of reaction of phenanthridine substituted with a desorption group on the 2-position and a hydrocarbon-metal compound to obtain di-substituted phenanthridine is shown below.

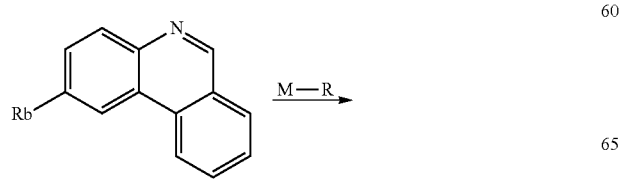

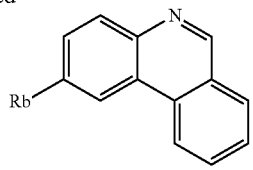

In the above formulae, Rb represents a desorption group, and R represents a hydrocarbon substituent.

By using the manufacturing method of the invention, the compound represented by formula (10) can be obtained in a high yield as compared with using conventional methods.

Rb represents a desorption group, which is the same with Rb in formula (a), and R represents a hydrocarbon substituent, which is the same with $Ra_2$ in formula (10).

As the examples of the desorption groups, generally used desorption groups, e.g., an alkylsulfonyloxy group, an arylsulfonyloxy group, a fluorine atom, a chlorine atom, a bromine atom and an iodine atom are exemplified, and a bromine atom is preferred.

R represents a hydrocarbon substituent, the example of which preferably includes an alkyl group having 1 to 10 carbon atoms, more preferably methyl, ethyl, n-propyl, isopropyl, n-butyl, t-butyl and neopentyl, and still more preferably neopentyl.

When n1 in formula (10) is 1, for example, the compound can be synthesized as follows.

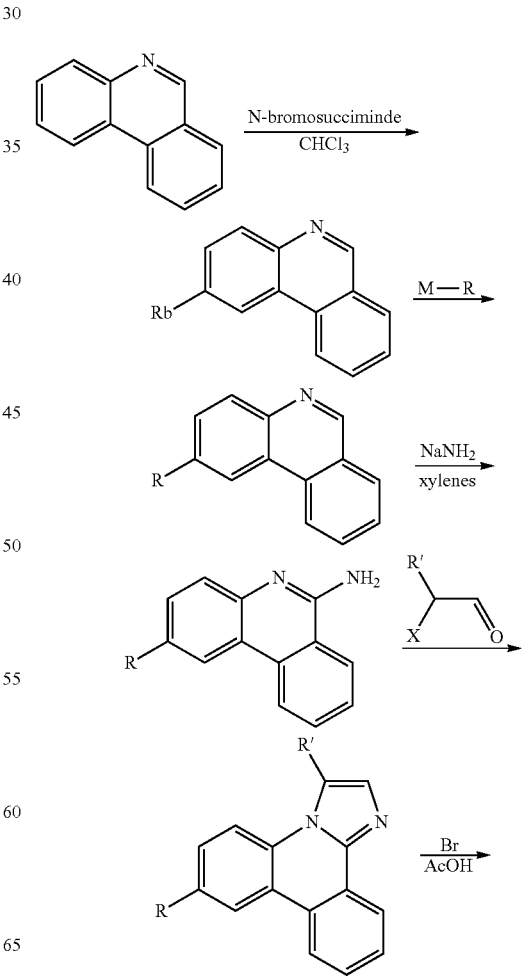

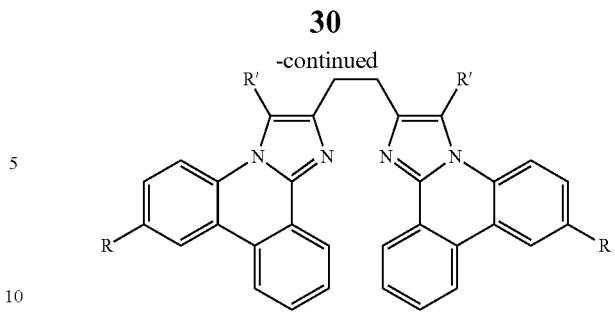
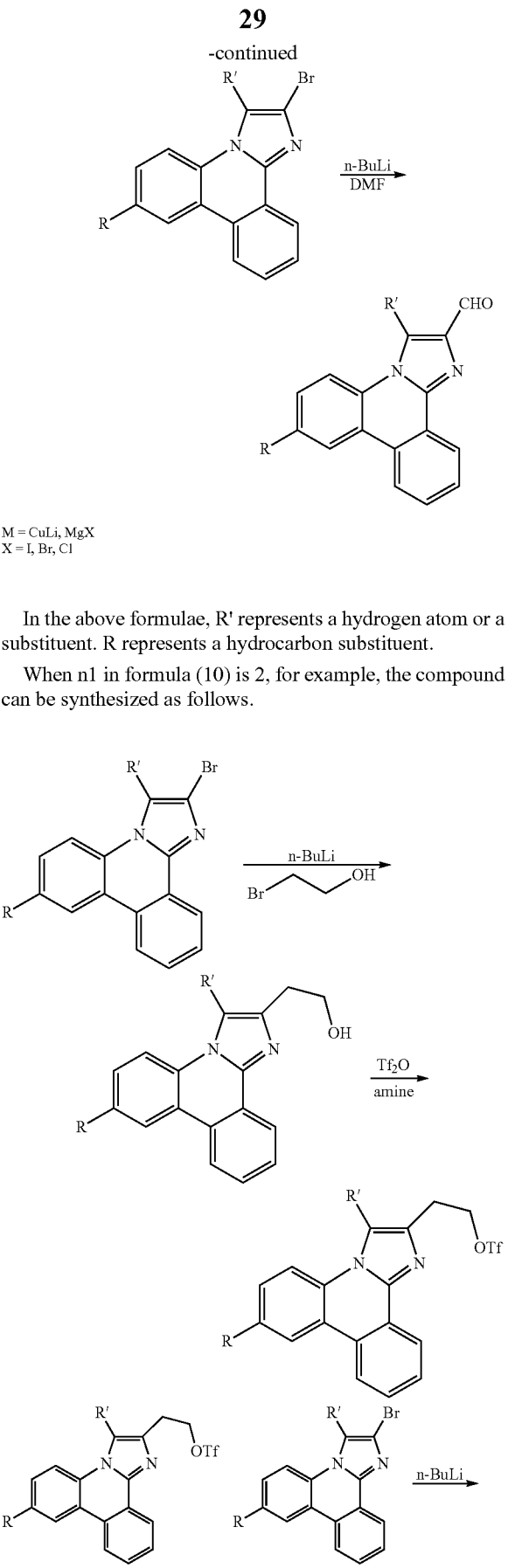

M = CuLi, MgX
X = I, Br, Cl

In the above formulae, R' represents a hydrogen atom or a substituent. R represents a hydrocarbon substituent.

When n1 in formula (10) is 2, for example, the compound can be synthesized as follows.

In the above formulae, R' represents a hydrogen atom or a substituent. R represents a hydrocarbon substituent.

As described above, the compound represented by formula (10) can be used as the intermediate of the compound represented by formula (1). That is, the metal complex of the compound represented by formula (10) can be obtained by coordination of the compound represented by formula (10) with a metal compound.

For example, the metal complex of the compound represented by formula (10) can be obtained at room temperature or lower or by heating (besides ordinary heating, a means of heating by microwave is also effectual) a ligand or a dissociated product thereof and a metal compound in the presence of a solvent (e.g., halogen-based solvents, alcohol-based solvents, ether-based solvents, ester-based solvents, ketone-based solvents, nitrile-based solvents, amide-based solvents, sulfone-based solvents, sulfoxide-based solvents, hydrocarbon-based solvents, water, and the like are exemplified), or in the absence of a solvent, in the presence of a base (various inorganic and organic bases e.g., sodium methoxide, potassium t-butoxy, triethylamine, potassium carbonate, and the like are exemplified), or in the absence of a base.

Organic Electroluminescence Device:

The organic electroluminescence device in the invention will be described in detail below.

The organic electroluminescence device in the invention is an organic electroluminescence device having a light emitting layer between a pair of electrodes, and having a layer containing a compound represented by formula (1).

In the organic electroluminescence device in the invention, the light emitting layer and the layer containing the compound represented by formula (1) are organic layers, and the device may have two or more organic layers in addition to these layers. It is preferred that the layer containing the compound represented by formula (1) is the light emitting layer.

From the nature of the 1 electroluminescence device, it is preferred that at least one electrode of the anode and cathode is transparent or translucent.

FIG. 1 shows an example of the constitution of the organic electroluminescence device according to the invention. Organic electroluminescence device 10 shown in FIG. 1 according to the invention comprises substrate 2 having thereon light emitting layer 6 between anode 3 and cathode 9. Specifically, hole injecting layer 4, hole transporting layer 5, electron blocking layer 6, light emitting layer 7, and electron transporting layer 8 are laminated in this order between anode 3 and cathode 9.

Constitution of Organic Layers:

The layer configuration of the organic layer is not particularly limited and may be appropriately selected according to the use and purpose of the organic electroluminescence device but is preferably formed on the transparent electrode or back plate. In this case, the organic layer is formed on the front surface or one surface of the transparent electrode or back plate.

The shape, size, thickness and the like of the organic layer are not particularly limited and may be appropriately selected according to the purpose.

As the specific layer constitutions, the following are exemplified but the invention is not restricted to these constitutions.

Anode/hole transporting layer/light emitting layer/electron transporting layer/cathode Anode/hole transporting layer/blocking layer/light emitting layer/electron transporting layer/cathode Anode/hole transporting layer/blocking layer/light emitting layer/electron transporting layer/electron injecting layer/cathode Anode/hole injecting layer/hole transporting layer/blocking layer/light emitting layer/electron transporting layer/cathode Anode/hole injecting layer/hole transporting layer/blocking layer/light emitting layer/electron transporting layer/electron injecting layer/cathode Anode/hole injecting layer/hole transporting layer/blocking layer/light emitting layer/blocking layer/electron transporting layer/electron injecting layer/cathode The organic layers are not especially restricted, but a hole injecting layer, a hole transporting layer, an electron injecting layer, an electron transporting layer, a hole blocking layer, an electron blocking layer, an exciton blocking layer, and a protective layer may be provided besides the light emitting layer. Each of these layers may combine its own function with functions of other layers.

As the embodiment of lamination of organic layers in the invention, an embodiment of lamination in the order from the anode side of a hole transporting layer, a light emitting layer and an electron transporting layer is preferred. Further, a charge blocking layer and the like may be provided between a hole transporting layer and a light emitting layer, or between a light emitting layer and an electron transporting layer. A hole injecting layer may be provided between the anode and a hole transporting layer, and an electron injecting layer may be provided between the cathode and an electron transporting layer. Incidentally, each layer may be divided to a plurality of secondary layers.

Each element constituting the device of the invention will be described in detail below.

Substrate:

The substrate for use in the present invention is preferably a substrate which does not scatter or attenuate the light emitted from the organic layer. When the substrate is made from an organic material, it is preferable that the organic material has excellent heat resistance, dimensional stability, solvent resistance, electrical insulation and workability.

Anode:

The anode is usually sufficient if it has a function as an electrode of supplying a hole to the organic layer. The shape, structure, size and the like thereof are not particularly limited, and the anode material may be appropriately selected from known electrode materials according to the use or purpose of the luminescence device. As described above, the anode is usually provided as a transparent anode.

Cathode:

The cathode is usually sufficient if it has a function as an electrode of injecting an electron in the organic layer. The shape, structure, size and the like thereof are not particularly limited, and the cathode material may be appropriately selected from known electrode materials according to the use or purpose of the luminescence device.

Regarding the substrate, anode and cathode, descriptions in JP-A-2008-270736, paragraphs [0070] to [0089] can be applied to the invention.

Organic Layers:

The organic layers in the invention are described below.

The organic layers include a light emitting layer and, as organic layers other than the light emitting layer, as described above, a hole transporting layer, an electron transporting layer, a hole blocking layer, an electron blocking layer, a hole injecting layer, and an electron injecting layer are exemplified.

Formation of Organic Layers:

In the organic electroluminescence device of the present invention, each organic layer may be suitably formed by any of a dry deposition method such as vapor deposition and sputtering, a transfer method, a printing method and the like.

Light Emitting Layer:

The light emitting layer is a layer having functions to receive, at the time of electric field application, holes from the anode, hole injecting layer or hole transporting layer, and receive electrons from the cathode, electron injecting layer or electron transporting layer, and offer the field of recombination of holes and electrons to emit light.

In the present invention, the light emitting layer may be composed of only a light emitting material or may have a mixed layer configuration of a host material and a light emitting material. The light emitting material may be either a fluorescent material or a phosphorescent material and as for the dopant, one kind of a dopant or two or more kinds of dopants may be used. The host material is preferably a charge transport material. As for the host material, one kind of a host material or two or more kinds of host materials may be used, and examples of this configuration include a configuration where an electron transporting host material and a hole transporting host material are mixed. Also, the light emitting layer may contain a material having no charge transport property and being incapable of producing luminescence. It is preferred that the host material and the compound represented formula (1) as the light emitting material are used in the light emitting layer.

Furthermore, the light emitting layer may be a single layer or a multilayer composed of two or more layers. In the case of a plurality of light emitting layers, the compounds represented by formula (1) may be contained in two or more light emitting layers. Also, respective light emitting layers may produce luminescence in different colors.

The host material to be used with the compound represented by formula (1) may be a hole transporting host material or an electron transporting host material, but a hole transporting host material is preferred.

Fluorescent Material:

Examples of a fluorescent material usable in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne derivatives, various kinds of complexes typified by complexes of 8-quinolinol derivatives and complexes of pyrromethene derivatives, polymeric compounds such as polythiophene, polyphenylene and polyphenylenevinylene, and compounds like organic silane derivatives.

Phosphorescent Material:

Examples of the phosphorescent material which can be used in the present invention include, other than the compounds represented by formula (1), phosphorescent compounds described in patent documents such as U.S. Pat. No. 6,303,238B1, U.S. Pat. No. 6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635 and JP-A-2007-96259. Examples of luminescent dopants which are far preferred among those compounds include the Ir complexes, the Pt complexes, the Cu complexes, the Re complexes, the W complexes, the Rh complexes, the Ru complexes, the Pd complexes, the Os complexes, the Eu complexes, the Tb complexes, the Gd complexes, the Dy complexes and the Ce complexes. Of these complexes, Ir complexes, the Pt complexes and the Re complexes are particularly preferable, notably Ir complexes, the Pt complexes and the Re complexes each having at least one kind of coordination bond selected from metal-carbon, metal-nitrogen, metal-oxygen and metal-sulfur coordinate bonds. In terms of luminous efficiency, durability under driving, chromaticity and so on, the Ir complexes, the Pt complexes and the Re complexes each having a polydentate ligand, including a tridentate ligand or higher, are preferred over the others.

The content of the phosphorescent material in the light emitting layer is preferably from 0.1 to 50 mass %, more preferably from 0.2 to 50 mass %, still more preferably from 0.3 to 40 mass %, and most preferably from 5 to 30 mass %, based on the total mass of the light emitting layer.

The content of the phosphorescent material which can be used in the invention (the compound represented by formula (1) and/or phosphorescent material to be used in combination) is preferably in the range of 0.1% by mass or more and 50% by mass or less based on the sum total of the amount of the light emitting layer, more preferably in the range of 1% by mass or more and 40% by mass or less, and most preferably in the range of 5% by mass or more and 30% by mass or less. In particular, in the range of 5% by mass or more and 30% by mass or less, the chromaticity of the light emission of the organic electroluminescence device is little in dependency on the addition concentration of the phosphorescent material.

It is most preferred for the organic electroluminescence device in the invention to contain at least one compound represented by formula (1) in an amount of 5 to 30% by mass based on the total amount of the light emitting layer.

Host Material:

The host material is a compound primarily injecting and transporting charge in a light emitting layer, which is a compound that does not substantially emit light. In the specification of the invention, the terms "does not substantially emit light" mean that the amount of light emission from the compound that does not substantially emit light is preferably 5% or less of the total amount of light emission of the device as a whole, more preferably 3% or less, and still more preferably 1% or less.

In the invention, it is preferred for the light emitting layer to contain a host material.

The concentration of the host material in the light emitting layer is not especially restricted, but the host material is preferably the main component (the component which accounts for the most content) in the light emitting layer, more preferably the concentration is 50% by mass or more and 99.9% by mass or less, still more preferably 50% by mass or more and 99.8% by mass or less, still yet preferably 60% by mass or more and 99.7% by mass or less, and most preferably 70% by mass or more and 95% by mass or less.

The glass transition point of the host material is preferably 60° C. or higher and 500° C. or lower, more preferably 70° C. or higher and 300° C. or lower, and still more preferably 90° C. or higher and 250° C. or lower.

The fluorescent wavelength of the host material contained in the light emitting layer of the invention in the state of a film is preferably in the range of 400 nm or more and 650 nm or less, more preferably in the range of 420 nm or more and 600 nm or less, and still more preferably in the range of 440 nm or more and 550 nm or less.

As the host materials contained in the light emitting layer in the invention, e.g., materials having a carbazole structure, materials having a diarylamine structure, materials having an indole structure, materials having a pyridine structure, materials having a pyrazine structure, materials having a triazine structure, materials having an arylsilane structure, and materials described later in the items of hole injecting layer, hole transporting layer, electron injecting layer and electron transporting layer are exemplified.

As the host materials for use in the invention, e.g., the compounds disclosed in JP-A-2002-100476, paragraphs [0113] to [0161] and JP-A-2004-214179, paragraphs [0087] to [0098] can be preferably used, but the invention is not restricted to these compounds.

It is preferred for the light emitting layer to contain a compound represented by formula (1) and further a host material. The host material may be either a hole transporting host material or an electron transporting host material, but a hole transporting host material is preferably used. The host material for use in the invention is preferably a compound represented by the following formula (4-1) or (4-2).

In the invention, it is preferred that the light emitting layer contains a compound represented by formula (1) and further at least either one of a compound represented by formula (4-1) or (4-2).

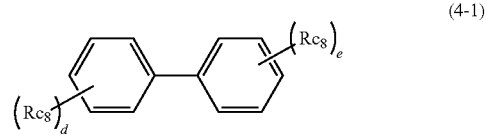

(4-1)

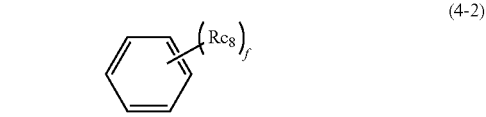

(4-2)

In formulae (4-1) and (4-2), each of d and e represents an integer of 0 to 3, and at least either is 1 or more. f represents an integer of 1 to 3. $Rc_8$ represents a carbazole group represented by the following formula (5).

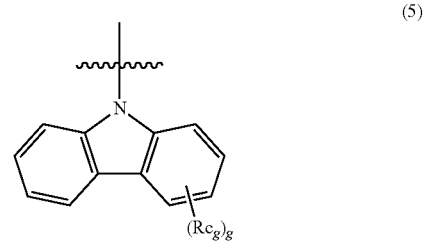

(5)

In formula (5), each Rc$_9$ independently represents a substituent. g represents an integer of 0 to 8.

Each Rc$_9$ independently represents a substituent, specifically a halogen atom, an alkoxy group, a cyano group, a nitro group, an alkyl group, an aryl group or a heterocyclic group, and preferably an alkyl group having 10 or less carbon atoms, or a substituted or unsubstituted aryl group having 10 or less carbon atoms.

g represents an integer of 0 to 8, and in view of not shielding the carbazole structure too much, which has a charge transporting function, the integer is preferably 0 to 4. When the carbazole has a substituent, from the viewpoint of easy synthesis, the one having a substituent symmetrically is preferred.

In formula (4-1), it is preferred that Rc$_8$ is substituted on the meta-position to the substitution position of the other benzene ring. Substitution on the ortho-position results in great steric hindrance of adjacent substituents and the bond is liable to be cleaved and durability lowers. Further, when substitution is on the para-position, the molecule approaches a rigid bar-like shape and easily crystallized, so that the device is liable to be deteriorated on high temperature condition. Furthermore, in formula (4-2), when f is 2 or 3, Rc$_8$ is preferably substituted on the meta-position to each other from the same point.

When formulae (4-1) and (4-2) have hydrogen atoms, isotopes (deuterium atoms and the like) are also included in the hydrogen atoms. In such a case, all the hydrogen atoms in the compounds may be substituted with isotopes, or the compounds may be mixtures partially containing isotopes. Preferred are compounds in which Rc$_9$ in formula (5) is substituted with a deuterium atom, and especially preferably the following structures are exemplified.

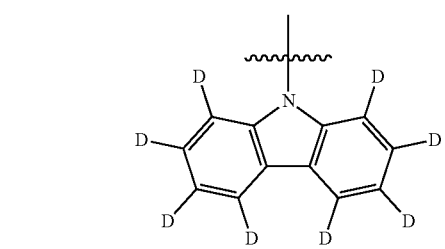

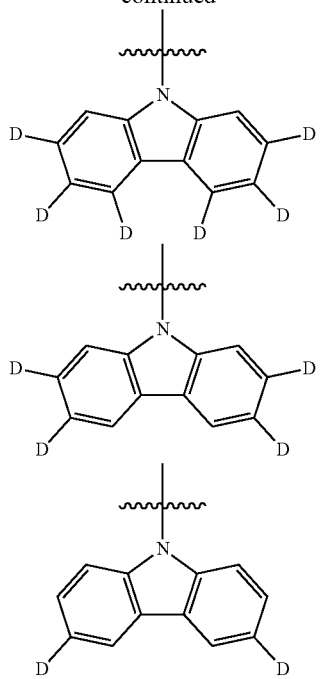

The atoms further constituting substituents also include the isotopes thereof.

It is preferred that a thin film of the compound represented by formula (4-1) or (4-2) is formed according to a vacuum deposition process, but a wet process such as solution coating can also be preferably used. The molecular weight of the compound is preferably 2,000 or less in view of deposition aptitude and solubility, more preferably 1,200 or less, and especially preferably 800 or less. In view of deposition aptitude, too small a molecular weight results in too small a vapor pressure, conversion from a gas phase to a solid phase does not occur and it becomes difficult to form an organic layer, so that the molecular weight is preferably 250 or more, and especially preferably 300 or more.

The specific examples of the compounds represented by any of formulae (4-1) and (4-2) are shown below, but the invention is not restricted thereto.

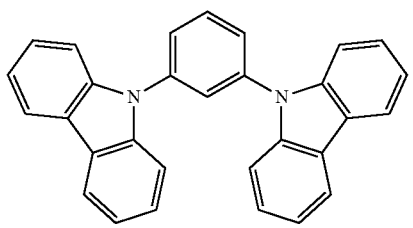

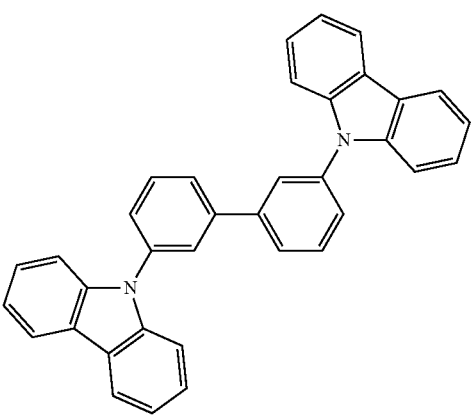

-continued
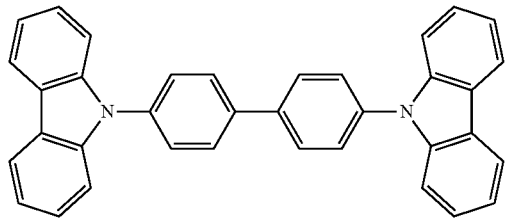
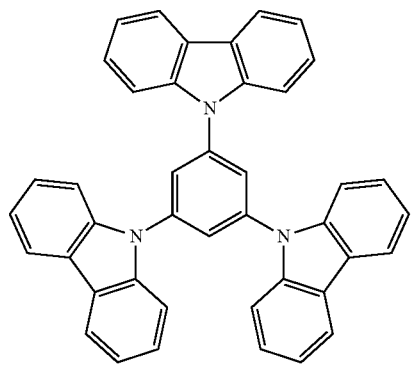
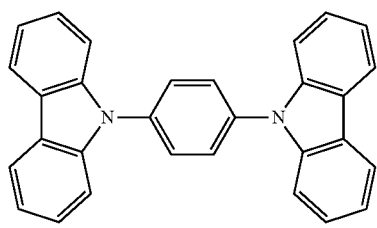
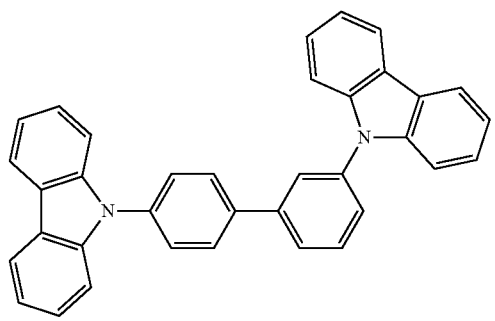
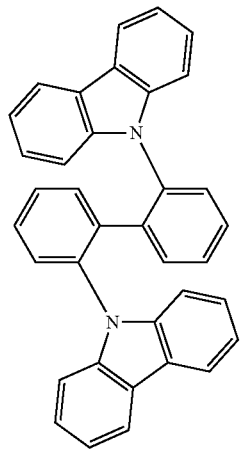
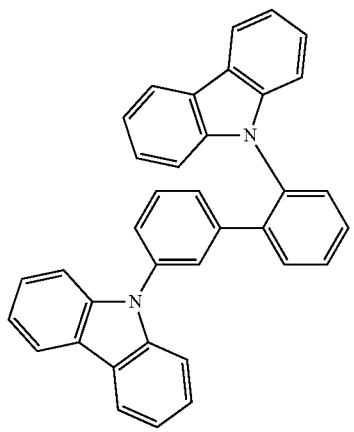
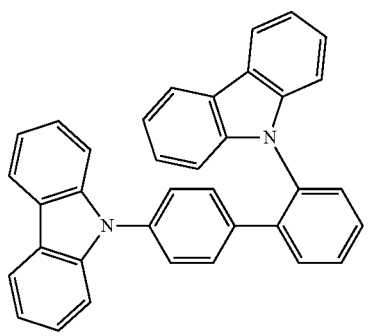
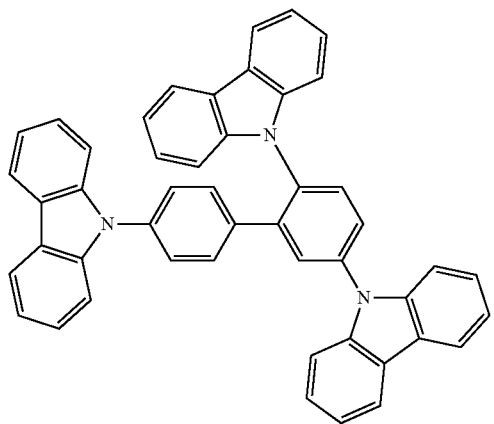
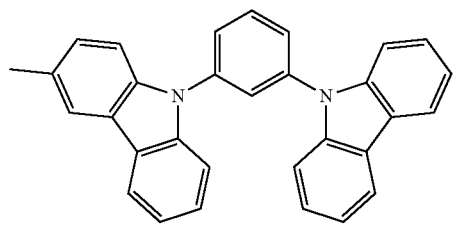

-continued
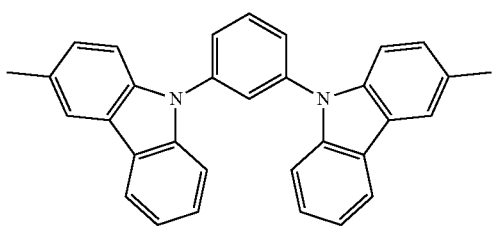 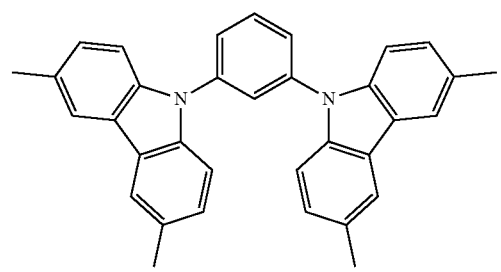
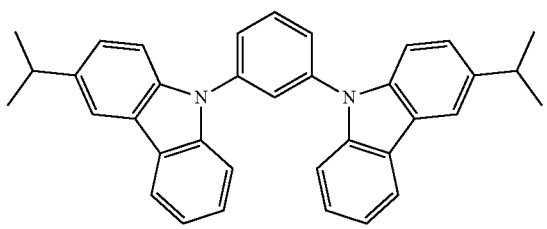 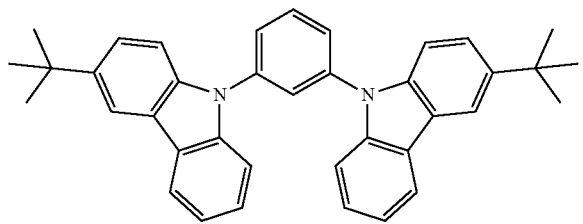
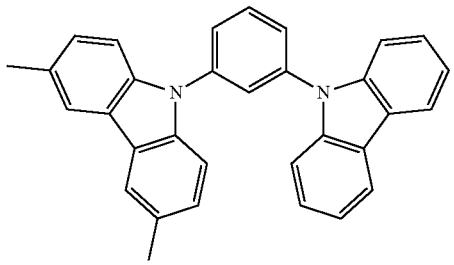 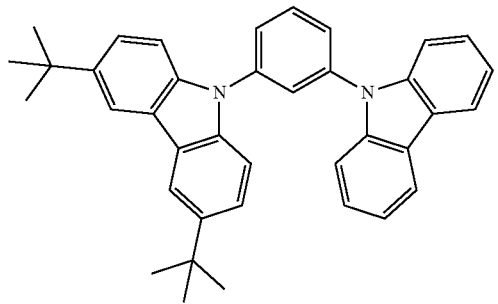
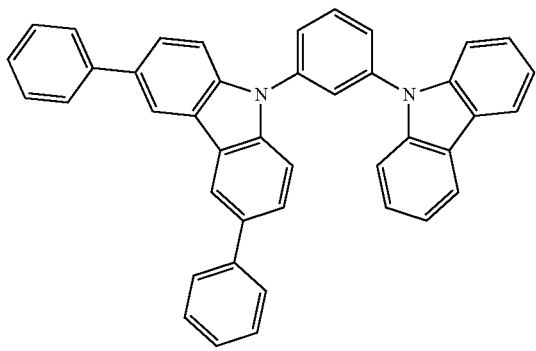 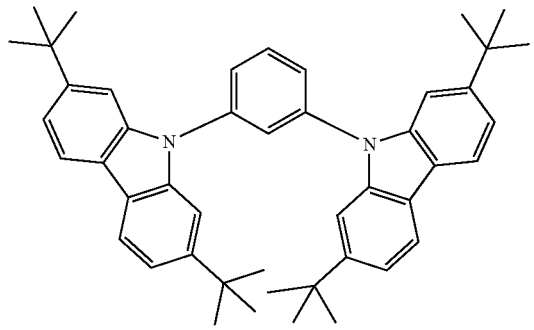
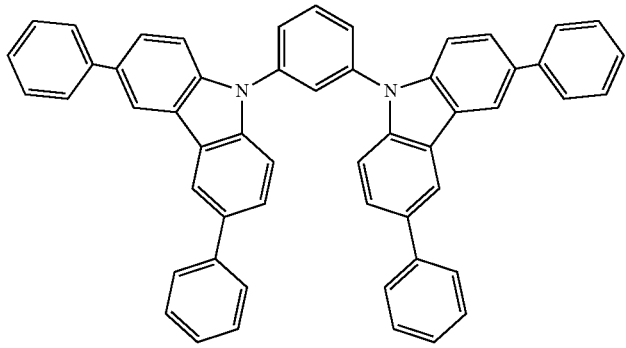 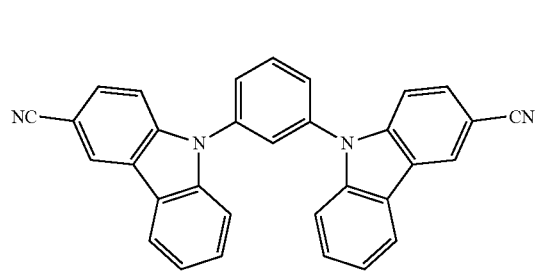

41 42
-continued
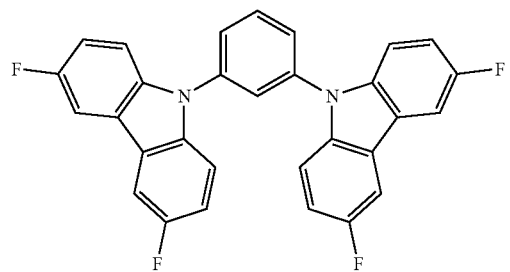 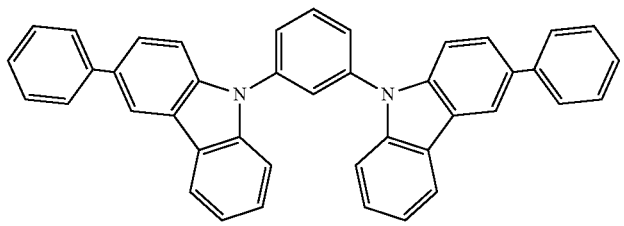
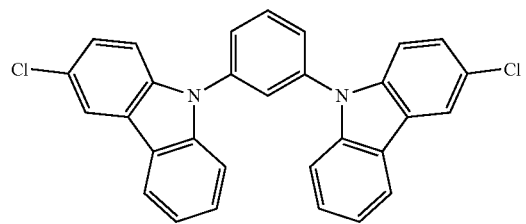 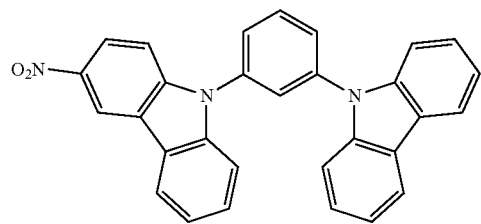
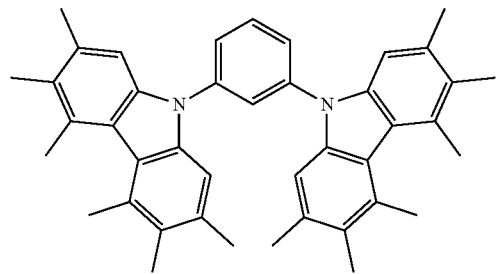 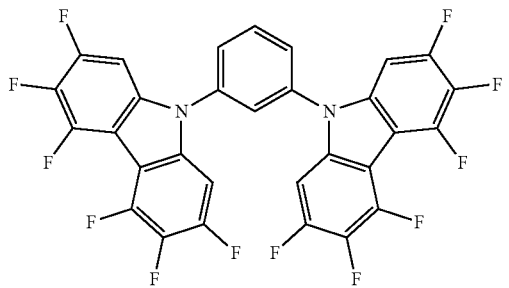
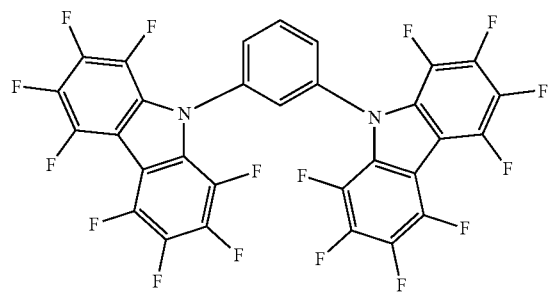 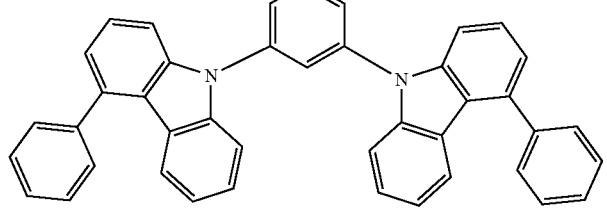
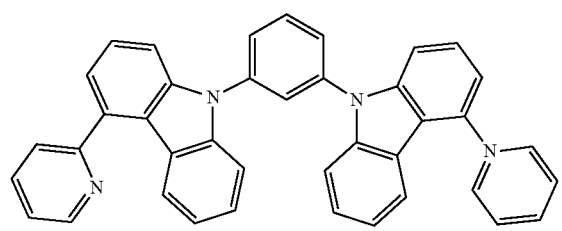 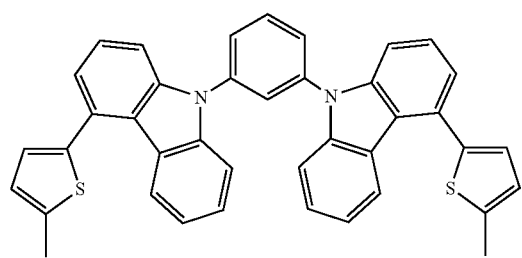

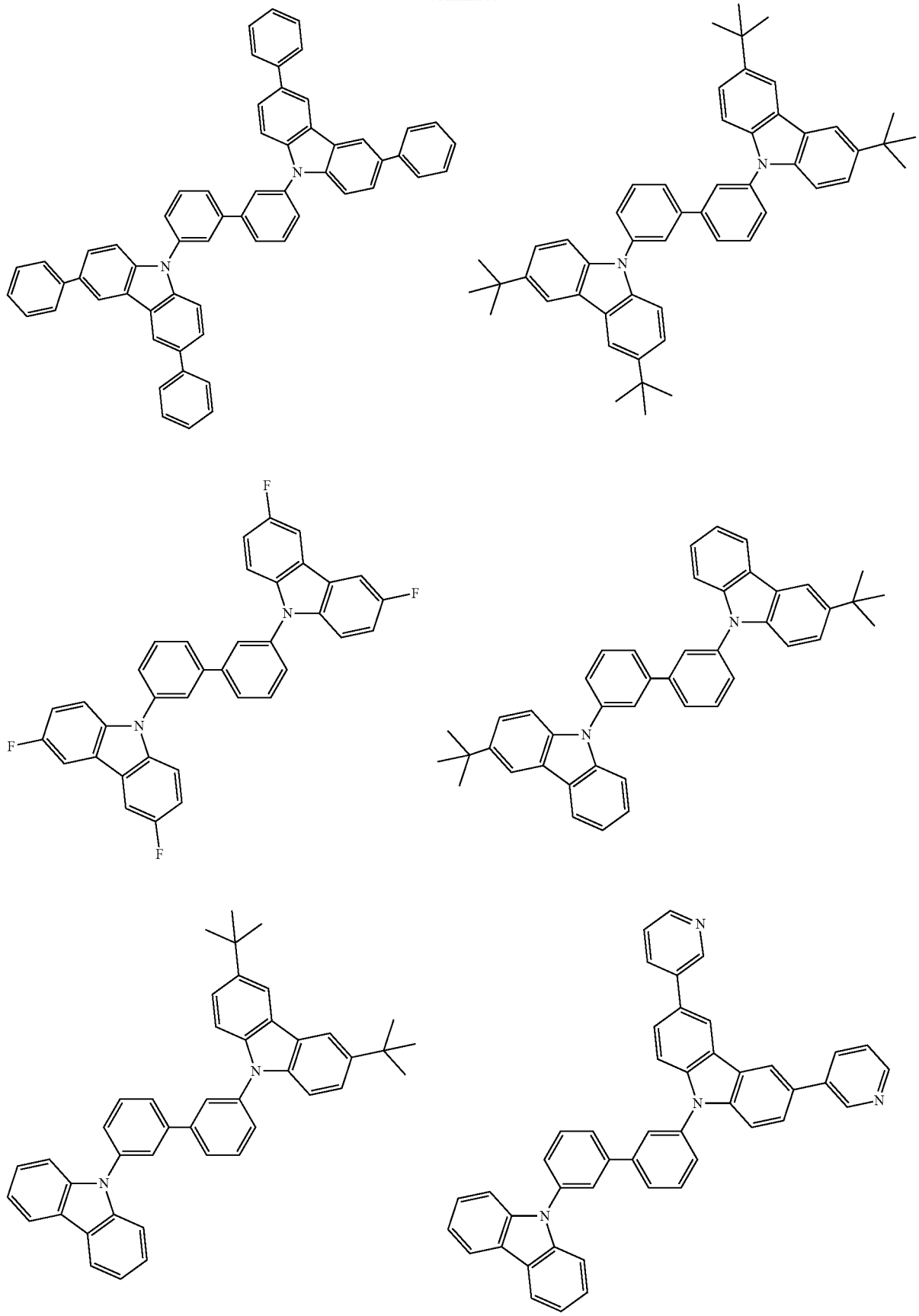

-continued

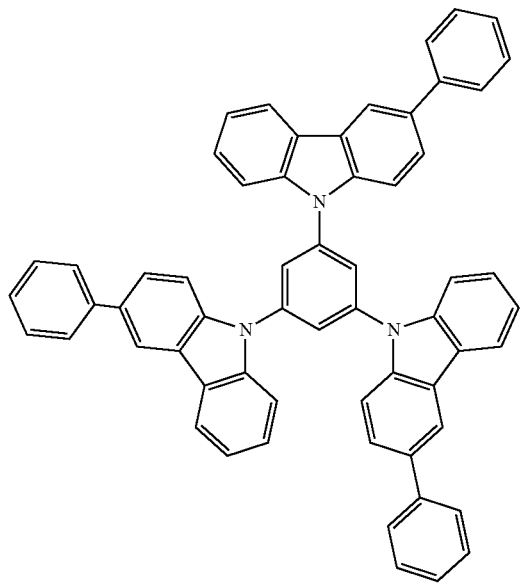
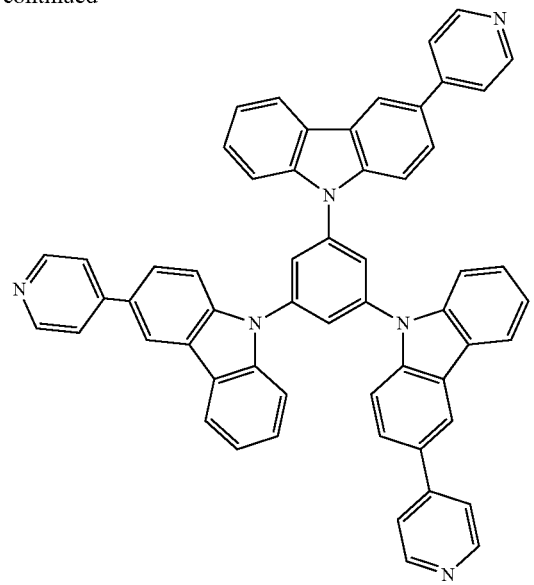

The compounds represented by formula (4-1) or (4-2) are more preferably the compounds shown below, or the compounds in which the hydrogen atoms are partially or entirely substituted with deuterium atoms.

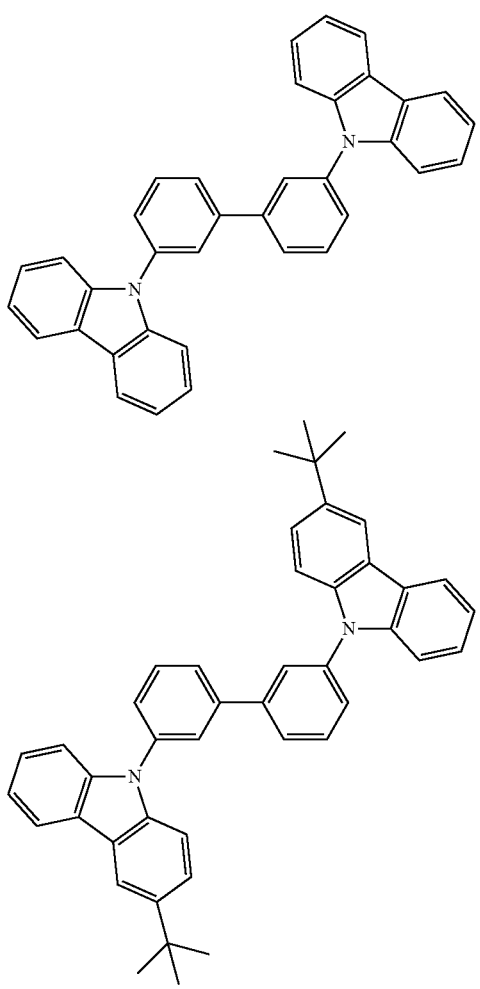

When the compound represented by formula (4-1) or (4-2) is introduced into the layer other than the light emitting layer (e.g., a charge transporting layer or the like), the compound is preferably contained in an amount of 10% by mass to 100% by mass in the layer, and more preferably 30% by mass to 100% by mass.

It is preferred for the organic electroluminescence device in the invention to further contain a hydrocarbon compound in the light emitting layer. Since the compound of the invention has a ligand having high planarity by planar tetradentate coordination, it is thought that the compound is susceptible to π orbit interaction from the neighboring host molecules and light emitting material. By the addition of a non-polar material such as a hydrocarbon compound to the light emitting layer, the interaction is reduced and unevenness of energy level is restrained, by which wave form of light emission becomes sharper, and a device showing high CIE chromaticity can be obtained. The hydrocarbon compound is saturated or unsaturated, and for giving deposition aptitude, a compound having a molecular weight of 900 or less is preferred. Further, it is necessary that the value of the triplet energy of the compound is greater than that of the light emitting material, so that it is preferred for the compound to contain saturated hydrocarbon such as alkane, cycloalkane, bicycloalkane or adamantane as the base structure, and a structure not directly linking to an aromatic ring is preferred.

The hydrocarbon compound is preferably a compound represented by the following formula (VI).

The compound represented by the following formula (VI) which is used in the organic electroluminescence device is excellent in chemical stability, little in deterioration such as decomposition of material during driving of the device, and reductions of efficiency of the organic electroluminescence device and duration of life of the device by the decomposed product of the material can be prevented.

The compound represented by formula (VI) is explained below.

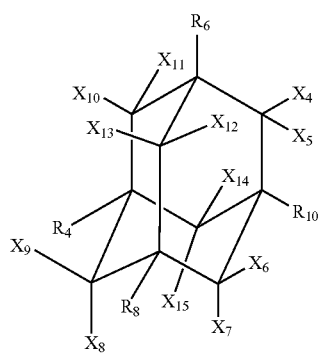

(VI)

In formula (VI), each of $R_4$, $R_6$, $R_8$, $R_{10}$, and $X_4$ to $X_{15}$ independently represents a hydrogen atom or a substituent. As the specific examples of the substituents, substituent group B is exemplified. Each of $R_4$, $R_6$, $R_8$, $R_{10}$, and $X_4$ to $X_{15}$ preferably represents a hydrogen atom, an alkyl group, or an aryl group.

In formula (VI), the alkyl group represented by $R_4$, $R_6$, $R_8$, $R_{10}$ and $X_4$ to $X_{15}$ may be substituted with an adamantane structure or an aryl structure and is preferably an alkyl group having a carbon number of 1 to 70, more preferably from 1 to 50, still more preferably from 1 to 30, yet still more preferably from 1 to 10, even yet still more preferably from 1 to 6, and most preferably a linear alkyl group having a carbon number of 2 to 6.

Examples of the alkyl group represented by each of $R_4$, $R_6$, $R_8$, $R_{10}$ and $X_4$ to $X_{15}$ in the formula (VI) include an n-$C_{50}H_{101}$ group, an n-$C_{30}H_{61}$ group, 3-(3,5,7-triphenyladamantane-1-yl)propyl group (number of carbon atoms: 31), a trityl group (number of carbon atoms: 19), 3-(adamantane-1-yl)propyl group (number of carbon atoms: 13), 9-decalyl group (number of carbon atoms: 10), a benzyl group (number of carbon atoms: 7), a cyclohexyl group (number of carbon atoms: 6), a n-hexyl group (number of carbon atoms: 6), an n-pentyl group (number of carbon atoms: 5), an n-butyl group (number of carbon atoms: 4), an n-propyl group (number of carbon atoms: 3), a cyclopropyl group (number of carbon atoms: 3), an ethyl group (number of carbon atoms: 2) and a methyl group (number of carbon atoms: 1).

The aryl group represented by each of $R_4$, $R_6$, $R_8$, $R_{10}$ and $X_4$ to $X_{15}$ in the formula (VI) may have as a substituent an adamantane structure or an alkyl structure, and the number of carbon atoms the aryl group has is preferably from 6 to 30, far preferably from 6 to 20, further preferably from 6 to 15, especially preferably from 6 to 10, the most preferably is 6.

Examples of the aryl group represented by each of $R_4$, $R_6$, $R_8$, $R_{10}$ and $X_4$ to $X_{15}$ in the formula (VI) include a 1-pyrenyl group (number of carbon atoms: 16), a 9-anthracenyl group (number of carbon atoms: 14), a 1-naphthyl group (number of carbon atoms: 10), a 2-naphthyl group (number of carbon atom: 10), a p-t-butylphenyl group (number of carbon atoms: 10), a 2-m-xylyl group (number of carbon atoms: 8), a 5-m-xylyl group (number of carbon atoms: 8), an o-tolyl group (number of carbon atoms: 7), a m-tolyl group (number of carbon atoms: 7), a p-tolyl group (number of carbon atoms: 7) and a phenyl group (number of carbon atoms: 6).

Although each of $R_4$, $R_6$, $R_8$ and $R_{10}$ in the formula (VI) may be either a hydrogen atom, or an alkyl group, or an aryl group, from the viewpoint that high glass transition temperatures are preferable, it is preferable that at least one of them is an aryl group, it is far preferable that at least two of them are aryl groups, and it is particularly preferable that 3 or 4 of them are aryl groups.

Although each of $X_4$ to $X_{15}$ in the formula (VI) may represent either a hydrogen atom, or an alkyl group, or an aryl group, it is preferable that each stands for a hydrogen atom or an aryl group, especially a hydrogen atom.

The organic electroluminescence devices are made using a vacuum deposition process or a solution coating process, and therefore, in terms of vacuum deposition suitability and solubility, the molecular weight of the compounds represented by the formula (VI) in the invention is preferably 2,000 or below, far preferably 1,200 or below, especially 1,000 or below. Also, from the viewpoint of vacuum deposition suitability, the molecular weight is preferably 250 or above, far preferably 350 or above, particularly preferably 400 or above. This is because, when the compounds have too low molecular weight, their vapor pressure becomes low and change from a vapor phase to a solid phase does not occur, and it is therefore difficult for the compounds to form organic layers.

The compound represented by the formula (VI) is preferably in solid phase at room temperature (25° C.), far preferably solid phase in a range from room temperature to 40° C., especially preferably solid phase in a range from room temperature to 60° C.

In the case of using the compound which, though represented by the formula (VI), is not in solid phase at room temperature, it is possible to form a solid phase at ordinary temperatures by combining the compound with other substances.

It is necessary to use the compound represented by formula (VI) in the light emitting layer by controlling the amount so as not to inhibit a charge transporting property, and the compound represented by formula (VI) is preferably used in an amount of 0.1 to 70% by mass, more preferably 0.1 to 30% by mass, and especially preferably used in an amount of 0.1 to 25% by mass.

The compound represented by formula (VI) may be used alone, or two or more compounds represented by formula (VI) may be used in combination in an arbitrary proportion.

The specific examples of the compounds represented by formula (VI) are shown below, but the invention is not restricted to these compounds.

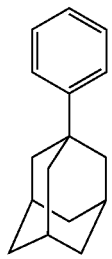

(1-1)

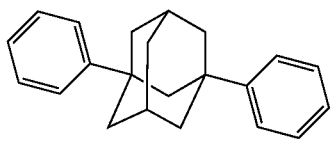

(1-2)

49
-continued
(1-3)
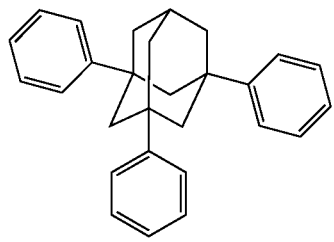
(1-4)
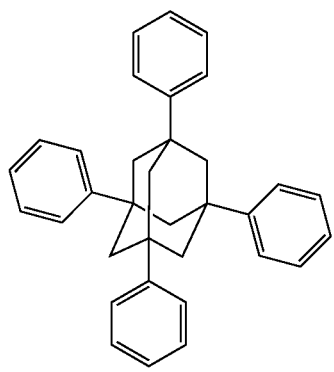
(1-5)
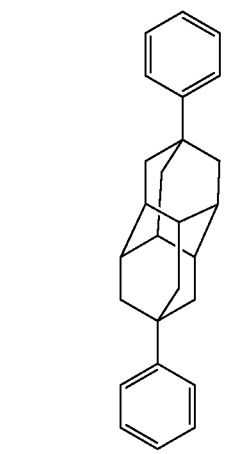
(1-6)
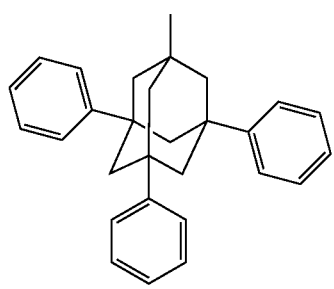
50
-continued
(1-7)
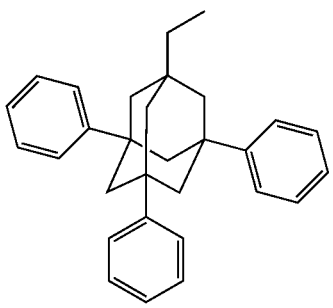
(1-8)
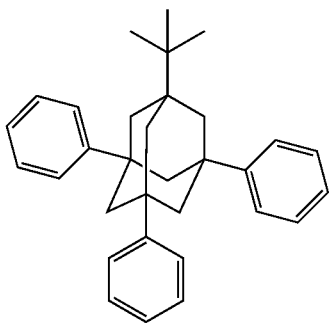
(1-9)
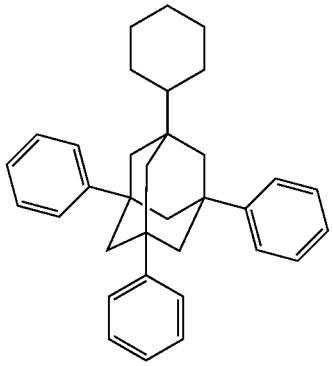
(1-10)
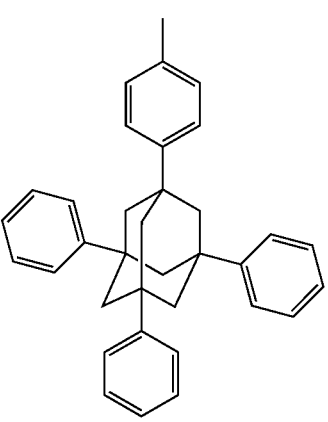

(1-11)
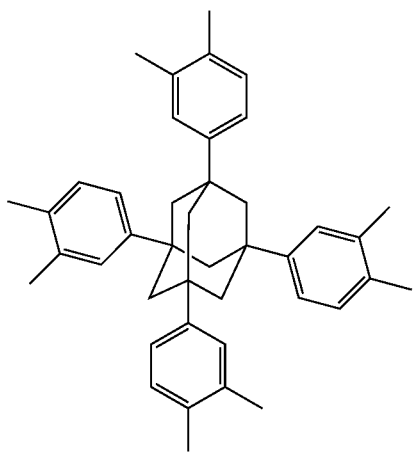
(1-12)
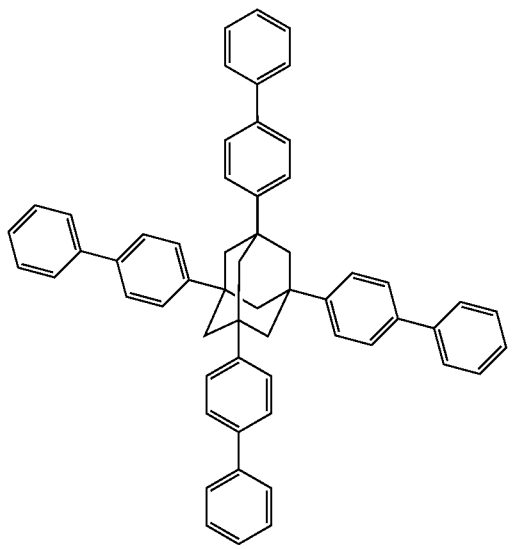
(1-13)
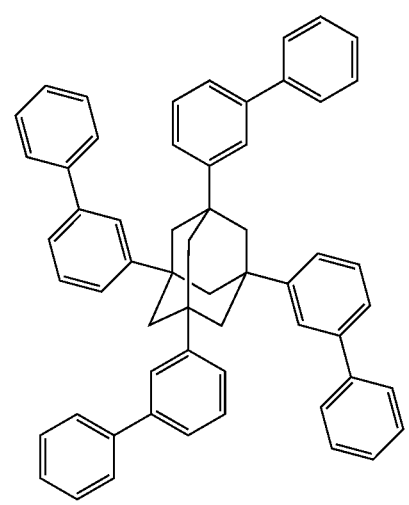
(1-14)
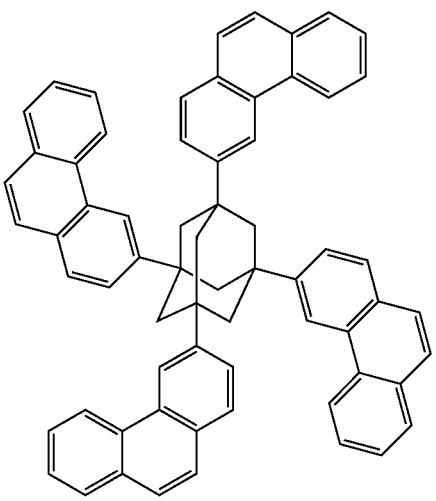
(1-15)
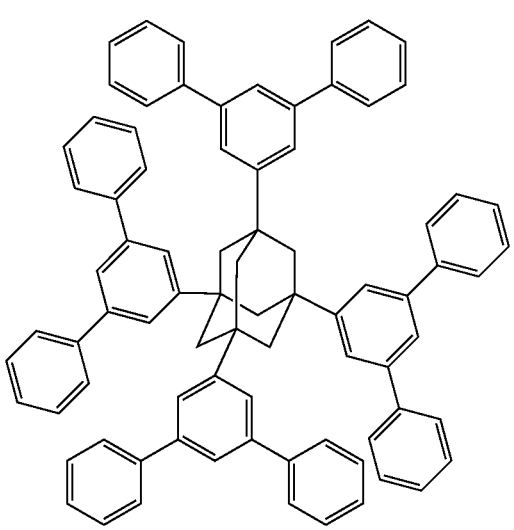
(1-16)
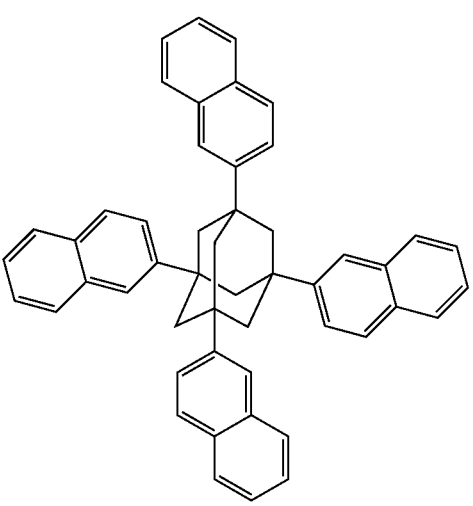

(1-17)
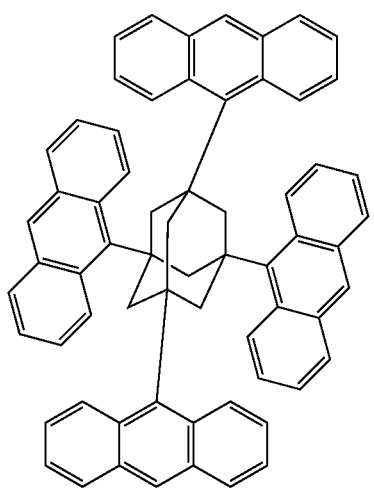
(1-18)
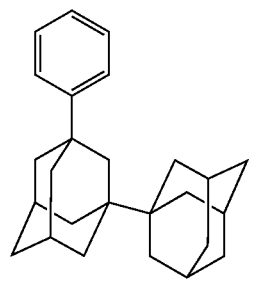
(1-19)
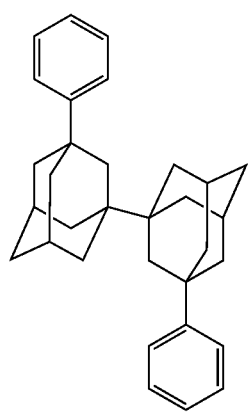
(1-20)
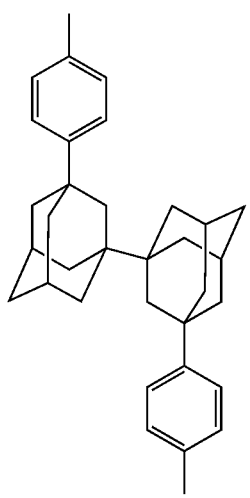
(1-21)
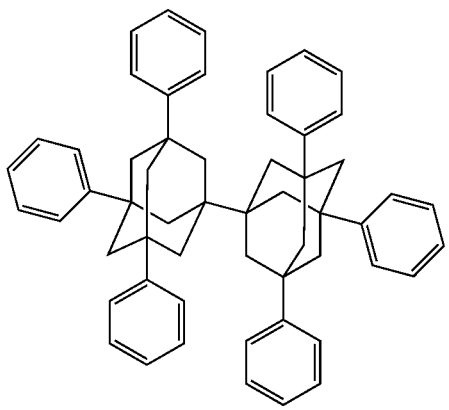
(1-22)
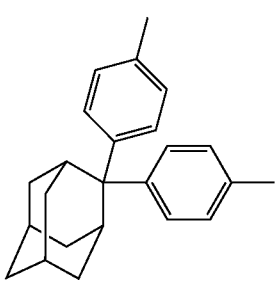

-continued
(1-23)
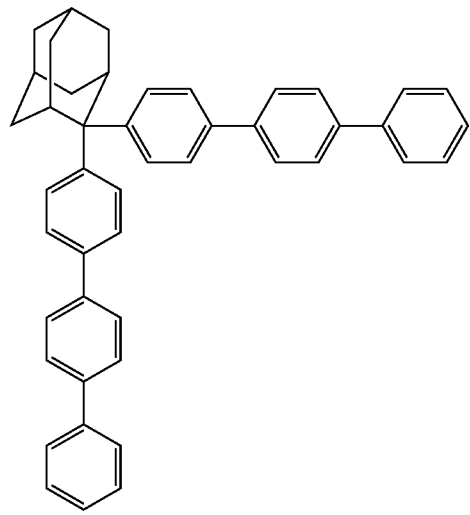
(1-24)
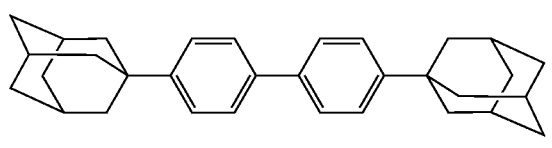
(1-25)
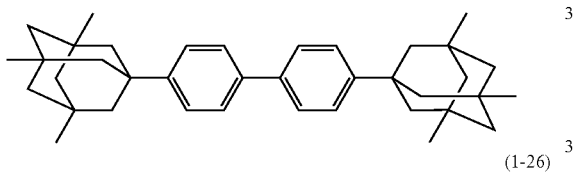
(1-26)
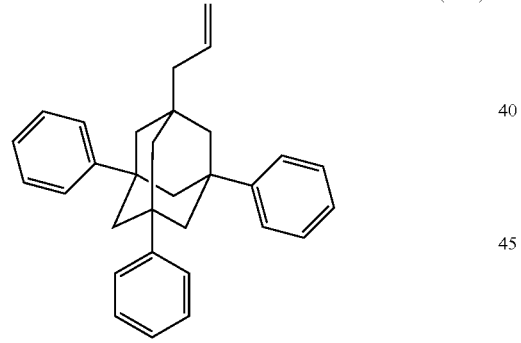
(1-27)
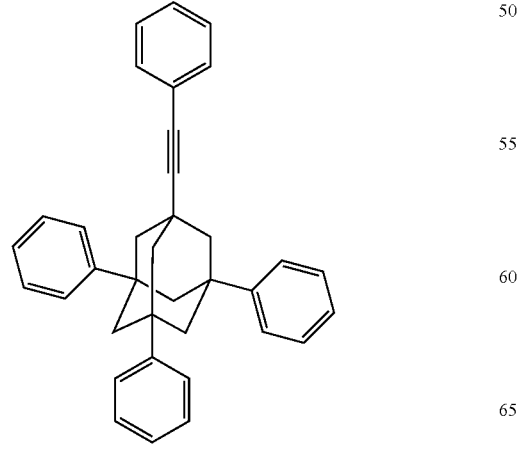
-continued
(1-28)
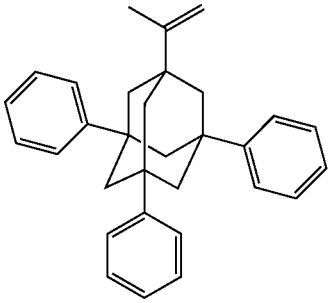
(1-29)
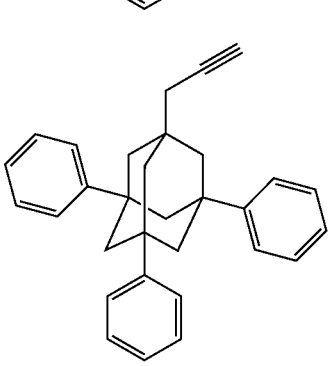
(1-30)
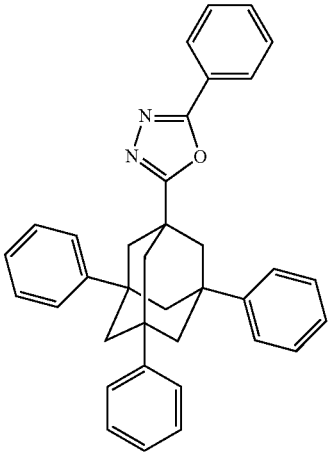
(1-31)
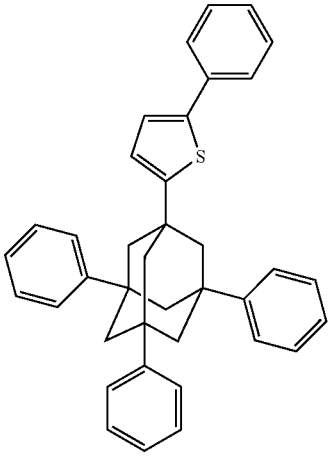

(1-32)
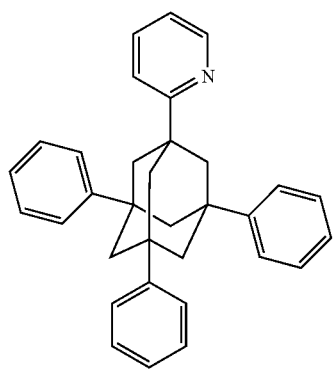
(1-33)
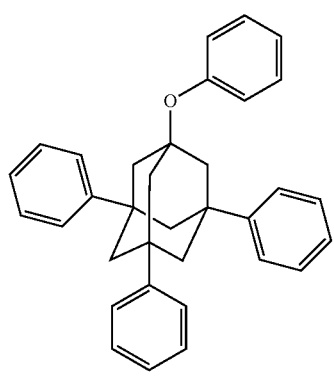
(1-34)
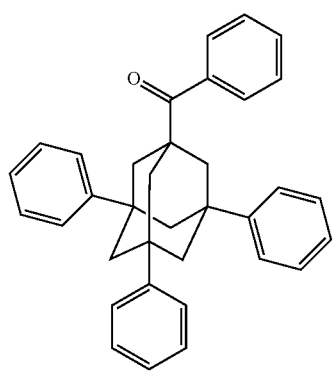
(1-35)
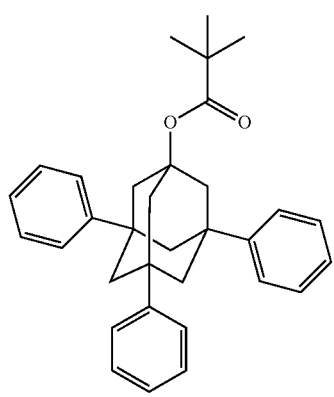
(1-36)
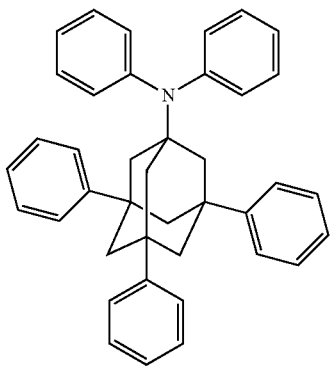
(1-37)
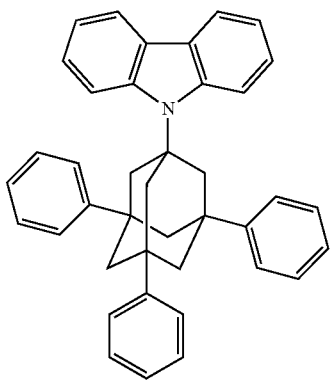
(1-38)
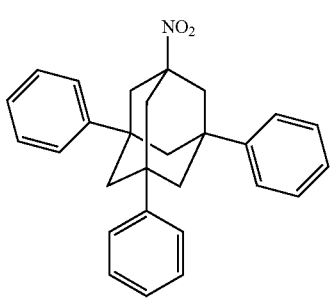
(1-39)
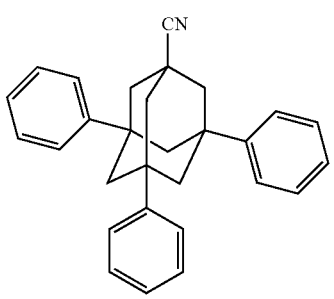
(1-40)
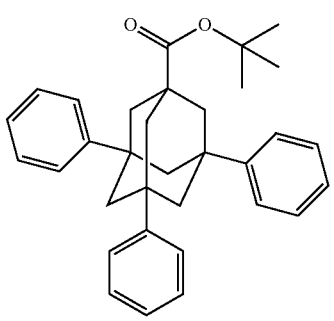

(1-41) 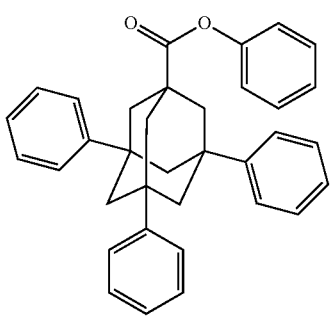

(1-46) 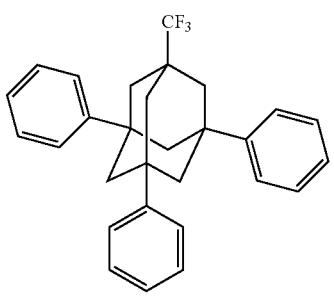

(1-42) 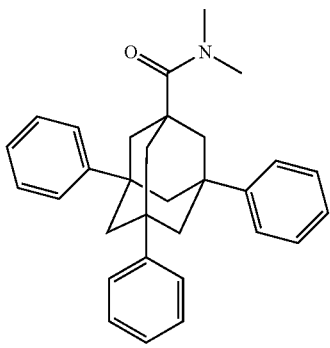

(1-47) 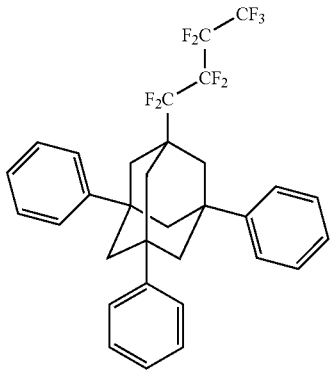

(1-43) 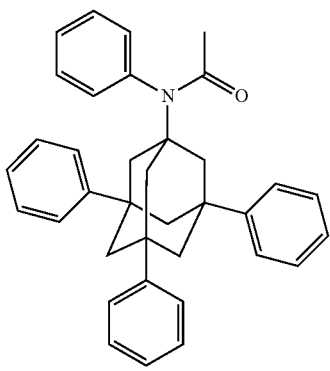

(1-48) 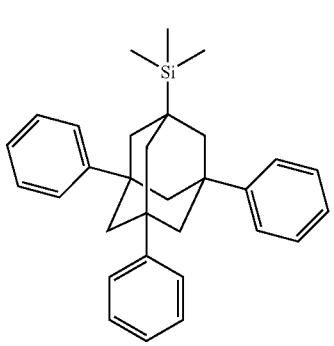

(1-44) 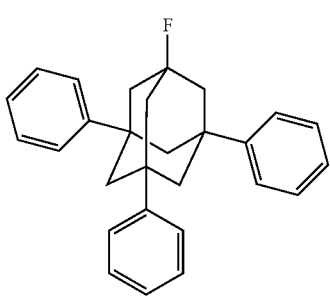

(1-49) 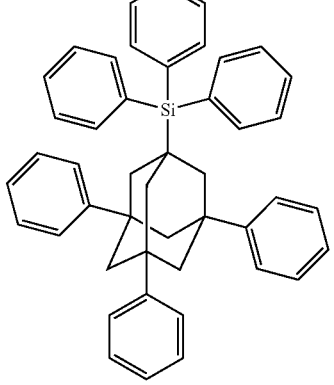

(1-45)

The compound represented by the formula (VI) can be synthesized by appropriately combining adamantane or haloadamantane with haloalkane or alkylmagnesium halide (Grignard reagent). For instance, it is possible to provide coupling between haloadamantane and haloalkane by use of indium (Reference 1). Alternatively, it is possible to convert haloalkane into an alkylcopper reagent and further to couple the reagent to Grignard reagent of an aromatic compound (Reference 2). Further, the coupling of haloalkane can also be performed using an appropriate arylboric acid and a palladium catalyst (Reference 3).

Reference 1: Tetrahedron Lett. 39, 9557-9558 (1998)
Reference 2: Tetrahedron Lett. 39, 2095-2096 (1998)
Reference 3: J. Am. Chem. Soc. 124, 13662-13663 (2002)

An adamantane structure having an aryl group can be synthesized by appropriately combining adamantane or haloadamantane with the corresponding arene or haloarene.

Additionally, even when defined substituents undergo changes under certain synthesis conditions in those production methods or they are unsuitable for carrying out those methods, the intended compounds can be produced with ease by adopting e.g. methods for protecting and deprotecting functional groups (T. W. Greene, Protective Groups in Organic Synthesis, John Wiley & Sons Inc. (1981)). Further, it is also possible to change the order of reaction steps, including a substituent introduction step, as appropriate, if needed.

The thickness of the light emitting layer is not particularly limited but usually, the thickness is preferably from 1 to 500 nm, more preferably from 5 to 200 nm, still more preferably from 10 to 100 nm.

Charge Transporting Layer:

The charge transporting layer is a layer having a function to receive electrons or holes from the electrode and transport electrons or holes on the light emitting layer side. The later-described hole injecting layer, hole transporting layer, electron transporting layer, electron injecting layer, electron blocking layer, and hole blocking layer are included therein.

In the organic electroluminescence device in the invention, it is preferred that the electrodes include an anode, the charge transporting layer is provided between the light emitting layer and the anode, and the charge transporting layer contains a carbazole compound.

The carbazole compound is preferably a carbazole compound represented by either the following formula (a) or (b).

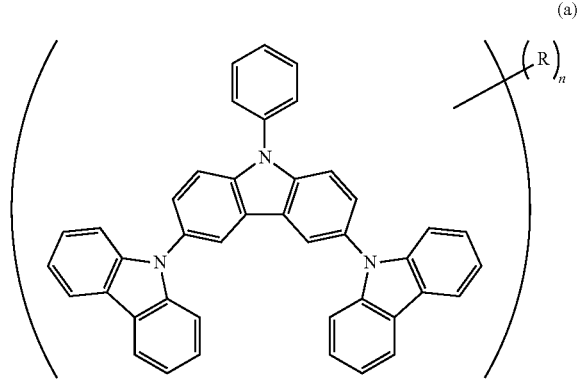

(a)

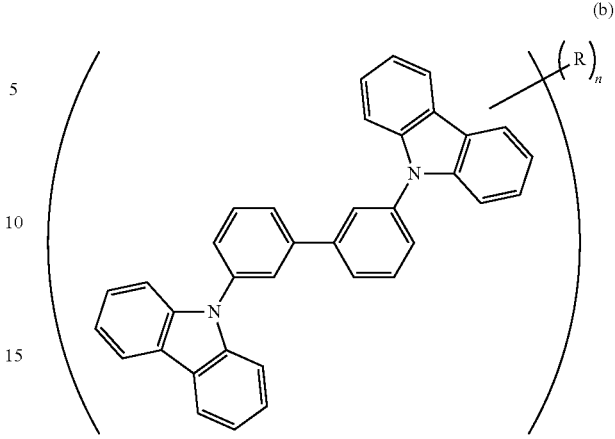

(b)

In formulae (a) and (b), R represents a substituent capable of substituting on the hydrogen atom of the carbazole compound, when there are two or more R's, each R may be the same with or different from every other R; and n represents an integer of 0 to 8.

Substituent group B is exemplified as the examples of R, and an alkyl group is preferred.

Concerning the carbazole compounds, synthesis by dehydrogenation aromatization after Aza-Cope arrangement of the condensation product of aryl hydrazine and cyclohexane derivative (L. F. Tieze and Th. Eicher, translated by Takano and Ogasawara, *Precision Organic Syntheses*, p. 339, published by Nanko-Do) is exemplified. Further, concerning the coupling reaction of the obtained carbazole compound and aryl halide compound using a palladium catalyst, the methods described in *Tetrahedron Letters*, Vol. 39, p. 617 (1998), ibid., Vol. 39, p. 2367 (1998), and ibid., Vol. 40, p. 6393 (1999) are exemplified. The reaction temperature and reaction time are not especially restricted and the conditions in the above documents are applied.

When the compound represented by formula (a) or (b) is used in the charge transporting layer, the compound represented by formula (a) or (b) is preferably contained in an amount of 50 to 100% by mass, more preferably in an amount of 80 to 100% by mass, and especially preferably in an amount of 95 to 100% by mass.

In the point of efficiency improvement, it is more preferred to use the compound represented by formula (a) as the charge transporting layer. It is presumably due to the fact that the compound represented by formula (a) is small in Ip as compared with carbazole compound such as mCP and does not prevent transportation of holes, as a result the quantity of charge recombination in the light emitting layer increases.

In the point of durability, it is more preferred to use the compound represented by formula (b) as the charge transporting layer. This is probably for the reason that the compound represented by formula (b) is great in the minimum triplet energy and the probability of receiving excitons generated in the light emitting layer by energy transfer is lowered, and the decomposition of the material of blocking layer is restrained.

Further, when the compound represented by formula (a) is used in two or more organic layers, it is preferred that the compound is used in the above range in each layer.

The compound represented by formula (a) or (b) may be used alone in any organic layer or two or more compounds represented by formula (a) or (b) may be used in combination in an arbitrary proportion.

The compound represented by formula (a) or (b) can be synthesized as follows. Most generally, concerning the carbazole compounds, synthesis by dehydrogenation aromatization after Aza-Cope arrangement of the condensation product of aryl hydrazine and cyclohexane derivative (L. F. Tietze and Th. Eicher, translated by Takano and Ogasawara, *Precision Organic Syntheses*, p. 339, published by Nanko-Do) is exemplified. Further, concerning the coupling reaction of the obtained carbazole compound and aryl halide compound using a palladium catalyst, the methods described in *Tetrahedron Letters*, Vol. 39, p. 617 (1998), ibid., Vol. 39, p. 2367 (1998), and ibid., Vol. 40, p. 6393 (1999) are exemplified. The reaction temperature and reaction time are not especially restricted and the conditions in the above documents are applied. The compound represented by formula (a) can also be synthesized, for example, according to the method disclosed in Japanese Patent 4140986, paragraphs on and after [0075].

The thickness of the charge transporting layer is preferably 1 to 500 nm, more preferably 3 to 200 nm, and still more preferably 5 to 100 nm.

The charge transporting layer may be a single layer structure having one or two or more materials described above, or may be a multilayer structure having plural layers of the same composition or different compositions.

As the substituent represented by R, substituent group B is exemplified, e.g., preferably a halogen atom, an alkoxy group, a cyano group, a nitro group, an alkyl group, an aryl group, or an aromatic heterocyclic group, and more preferably an alkyl group having 10 or less carbon atoms, or a substituted or unsubstituted aryl group having 10 or less carbon atoms.

n represents an integer of 0 to 8, preferably 0 to 4, and more preferably 0 to 2.

Hole Injecting Layer and Hole Transporting Layer:

The hole injecting layer and the hole transporting layer are provided between the anode and the light emitting layer, which are layers having functions of receiving holes from the anode or anode side and transporting the holes to the cathode side. Specifically, the hole injecting layer and hole transporting layer are preferably layers containing carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, porphyrin compounds, organic silane derivatives, carbon, etc.

The thickness of the hole injecting layer and hole transporting layer is each preferably 500 nm or less in view of lowering driving voltage.

The thickness of the hole transporting layer is preferably 1 to 500 nm, more preferably 5 to 200 nm, and still more preferably 5 to 100 nm. The thickness of the hole injecting layer is preferably 0.1 to 500 nm, more preferably 0.5 to 300 nm, and still more preferably from 1 to 200 nm.

The hole injecting layer and the hole transporting layer may have a single layer structure comprising one kind or two or more kinds of the above materials, or may be a multilayer structure comprising plural layers of the same composition or different compositions.

Electron Injecting Layer and Electron Transporting Layer:

The electron injecting layer and the electron transporting layer are provided between the cathode and the light emitting layer, which are layers having functions of receiving electrons from the cathode or cathode side and transporting the electrons to the anode side. Specifically, the electron injecting layer and the electron transporting layer are preferably layers containing various complexes represented by complexes of triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, aromatic cyclic tetracarboxylic anhydrides such as naphthalene and perylene, phthalocyanine derivatives, phenanthrene derivatives, phenanthroline derivatives, 8-quinolinol derivatives, complexes having metalphthalocyanine, benzoxazole or benzothiazole as the ligand, and organic silane derivatives.

The thickness of each of the electron injecting layer and the electron transporting layer is preferably 100 nm or less from the point of lowering the driving voltage.

The thickness of the electron transporting layer is preferably 1 to 100 nm, more preferably 5 to 50 nm, and still more preferably 10 to 30 nm. The thickness of the electron injecting layer is preferably 0.1 to 100 nm, more preferably 0.2 to 80 nm, and still more preferably 0.5 to 50 nm.

The electron injecting layer and the electron transporting layer may have a single layer structure comprising one or two or more kinds of the above materials, or may be a multilayer structure having plural layers of the same composition or different compositions.

Hole Blocking Layer:

The hole blocking layer is a layer having a function of blocking the holes transported from an anode side to the light emitting layer from passing on through to the cathode side. In the invention, the hole blocking layer can be provided as an organic layer adjacent to the light emitting layer in the cathode side.

Examples of an organic compound which forms the hole blocking layer include aluminum complexes such as aluminum(III)bis(2-methyl-8-quinolinato) 4-phenylphenolate (abbreviated to BAlq), carbazole derivatives, triazole derivatives, and phenanthroline derivatives such as 2,9-dimethyl-4,7-diphenyl-1,10-phenanthroline (abbreviated to BCP).

The thickness of the hole blocking layer is preferably from 1 nm to 500 nm, far preferably from 5 nm to 200 nm, further preferably from 10 nm to 100 nm.

The hole blocking layer may have either a single-layer structure made up of one or more than one material as recited above or a multiple-layer structure made up of two or more layers which are identical or different in composition.

—Electron Blocking Layer—

The electron blocking layer is a layer having a function of preventing the electrons transported from the cathode side to the light emitting layer from passing through to the anode side. In the invention, the electron blocking layer can be provided as an organic layer adjacent to the light emitting layer on the anode side.

As the examples of the compounds constituting the electron blocking layer, for instance, the hole transporting materials described above can be applied.

The thickness of the electron blocking layer is preferably from 1 nm to 500 nm, more preferably from 5 nm to 200 nm, still more preferably from 10 nm to 100 nm.

The electron blocking layer may have a single layer structure composed of one or more of the above materials or may be a multilayer structure composed of two or more layers having the same composition or different compositions.

Protective Layer:

In the present invention, the entire organic EL device may be protected by a protective layer.

As for the protective layer, the matters described in JP-A-2008-270736, paragraphs [0169] and [0170] can be applied to the present invention.

Sealing Case:

The device of the present invention may be entirely sealed using a sealing case.

As for the sealing container, the matters described in JP-A-2008-270736, paragraph [0171] can be applied to the present invention.

Luminescence of the device of the present invention can be obtained by applying a DC (if desired, an AC component may be contained) voltage (generally from 2 to 15 volts) or a DC current between the anode and the cathode.

As for the driving method of the device of the present invention, the driving methods described, for example, in JP-A-2-148687, JP-A-6-301355, JP-A-5-29080, JP-A-7-134558, JP-A-8-234685, JP-A-8-241047, Japanese Patent 2784615, and U.S. Pat. Nos. 5,828,429 and 6,023,308 can be applied.

Use of the Luminescence Device of the Invention:

The present luminescence devices can be used suitably for indication devices, displays, backlights, electrophotographic devices, illumination light sources, recording light sources, exposure light sources, readout light sources, sign, billboards, interior decorations or optical communications, especially preferably for devices driven in a region of high-intensity luminescence, such as illumination apparatus and display apparatus.

Next the present light luminous apparatus is explained by reference to FIG. 2.

The present light luminous apparatus incorporates any one of the present organic electroluminescence devices.

Figure 2:
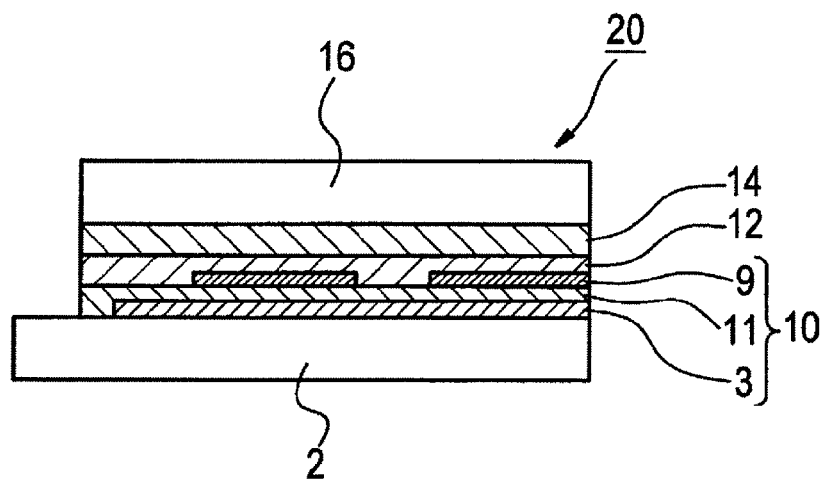
FIG. 2 is a schematic view showing an example of a light emitting apparatus according to the invention (a second embodiment).

FIG. 2 is a cross-sectional diagram schematically showing one example of the present light luminous apparatus.

The light luminous apparatus 20 in FIG. 2 includes a transparent substrate 2 (supporting substrate), an organic electroluminescence device 10, a sealing case 16 and so on.

The organic electroluminescence device 10 is formed by stacking on the substrate 2 an anode 3 (first electrode), an organic layer 11 and a cathode 9 (second electrode) in the order of mention. In addition, a protective layer 12 is superposed on the cathode 9, and on the protective layer 12 a sealing enclosure 16 is further provided via an adhesive layer 14. Incidentally, part of each of the electrodes 3 and 9, a diaphragm and an insulating layer are omitted in FIG. 2.

Herein, a light cure adhesive such as epoxy resin, or a thermosetting adhesive can be used for the adhesive layer 14. Alternatively, a thermosetting adhesive sheet may be used as the adhesive layer 14.

The present light emission apparatus has no particular restrictions as to its uses, and specifically, it can be utilized e.g. as not only illumination apparatus but also display apparatus of a television set, a personal computer, a mobile phone, an electronic paper or the like.

The illumination apparatus according to an embodiment of the present invention is described below by referring to FIG. 3.

Figure 3:
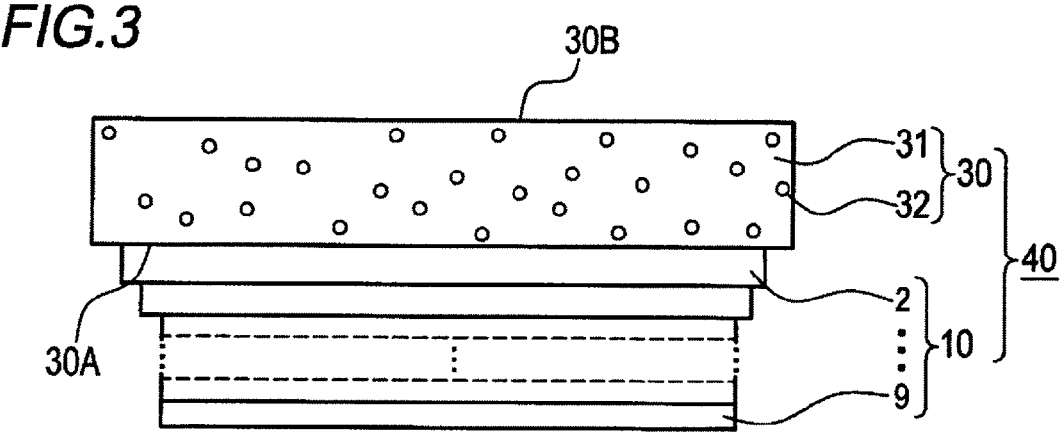
FIG. 3 is a schematic view showing an example of an illuminating apparatus according to the invention (a third embodiment).

The illumination apparatus 40 according to an embodiment of the present invention contains, as shown in FIG. 3, the above-described organic electroluminescence device 10 and a light scattering member 30. More specifically, the illumination apparatus 40 is configured such that the substrate 2 of the organic electroluminescence device 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particle 32 include a transparent resin fine particle. As the glass substrate and the transparent resin fine particle, a known product can be used for both. In such an illumination apparatus 40, when light emitted from the organic electroluminescence device 10 is incident on the light incident surface 30A of the scattering member 30, the incident light is scattered by the light scattering member and the scattered light is output as illuminating light from the light output surface 30B.

EXAMPLES

The invention will be described more specifically with reference to examples, but the invention is by no means restricted to these specific examples.

Synthesis Example 1

Exemplified compound G shown below is synthesized.

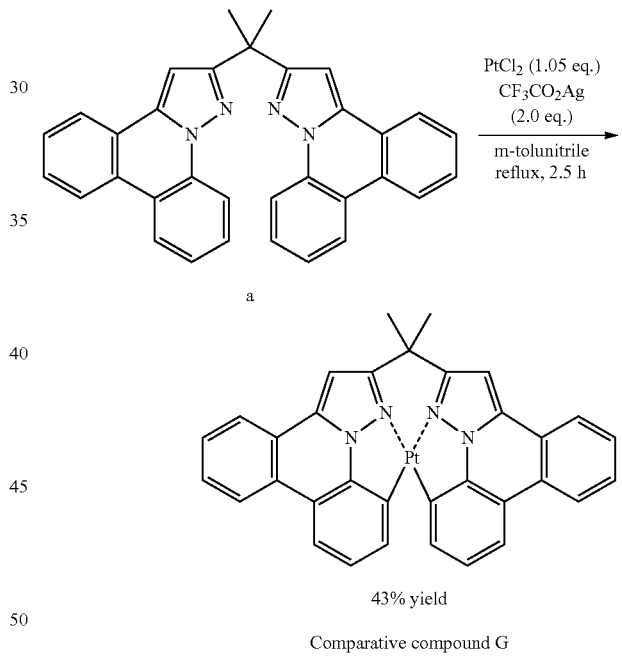

Compound a (40.0 mg, 83.9 mmol, 1.0 equivalent), platinum dichloride (23.4 mg, 88.0 mmol, 1.05 equivalents), and silver trifluoroacetate (37.0 mg, 167 mmol, 2.0 equivalents) are stirred in m-tolunitrile (5 mL) for 5 hours and 30 minutes on heating refluxing condition in nitrogen atmosphere. After concentration, drying and solidification of the reaction solution, the obtained residue is offered to silica gel column chromatography (hexane:$CH_2Cl_2$:=1:1). The obtained crude product is washed with ethyl acetate/methanol (1/2) to obtain 24.0 mg of a platinum complex as yellow powder. Yield: 43%

$^1$H-NMR (300 MHz, $CDCl_3$) δ: 2.06 (s, 6H), 7.09 (s, 2H), 7.55-7.75 (m, 6H), 8.09 (d, J=7.7 Hz, 2H), 8.18 (dd, J=7.7 Hz, 1.3 Hz, 2H), 8.26 (m, J (Pt—H)=51.2 Hz, 2H), 8.54 (d, J=7.5 Hz, 2H).

Manufacture of Device 1-1 of the Invention:

A glass substrate having an ITO film (manufactured by Geomatec Co., Ltd., surface resistance: 10Ω/□)) having a thickness of 0.5 mm and a size of 2.5 cm square is put in a washer and subjected to ultrasonic washing in 2-propanol, and then UV-ozone treatment for 30 minutes. The organic layers shown below are deposited on the transparent anode (ITO film) in sequence by a vacuum deposition method.

First layer: CuPc, layer thickness: 160 nm
Second layer: NPD, layer thickness: 10 nm
Third layer: light emitting material A (15% by mass), mCBP (85% by mass), layer thickness: 60 nm
Fourth layer: BAlq, layer thickness: 10 nm
Fifth layer: BCP (99% by mass) and Li (1% by mass), layer thickness: 20 nm Lithium fluoride in a thickness of 1.0 nm and metal aluminum in a thickness of 100 nm are deposited thereon in this order to obtain a cathode.

The obtained laminate is put in a glove box replaced with argon gas so as not to be in contact with air, and sealed with a stainless steel sealing can and a UV-curable type adhesive (XNR5516HV, manufactured by Nagase Chemtex Corporation) to obtain device 1-1 of the invention.

Manufacture of Devices 1-2 to 1-7 of the Invention and Comparative Devices 1 to 3:

Each device is manufactured in the same manner as in the manufacture of device 1-1 of the invention except for changing each constituting material in the third layer, i.e., light emitting layer material 1 as shown in Table 1 below. The numerals in light emitting layer materials 1 to 3 are corresponding to the numerals given to the exemplified compound.

Manufacture of Devices 2-1 to 2-4 of the Invention:

Each device is manufactured in the same manner as in the manufacture of device 1-1 of the invention except for depositing the material shown in Table 1 as "HTL" between the second layer and the third layer in a thickness of 10 nm.

Manufacture of Devices 3-1 to 3-5 of the Invention:

Each device is manufactured in the same manner as in the manufacture of device 1-1 of the invention except for depositing the composition in the third layer as shown in Table 1.

The light emitting efficiency and half life time of luminance of the obtained devices are measured and the efficiency and durability of the devices are evaluated. Each measurement is carried out as follows.

(a) Light Emitting Wavelength

DC voltage is applied to each device for light emission with source measure unit Model 2400 (manufactured by Toyo Corporation). The light emitting wavelength is measured with a spectrum analyzer PMA-11 (manufactured by Hamamatsu Photonics K.K.).

(b) Half Life Time of Luminance

DC voltage is applied to each device for light emission with source measure unit Model 2400 (manufactured by Toyo Corporation). The half life time of luminance at that time is measured with a luminometer BM-8 (manufactured by Topcon Corporation). Other devices are also measured in the same manner. Half life time at starting luminance 2,000 cd/m$^2$ of device 1-1 of the invention is taken as 100, and the value of each device as relative value on the basis of this value is shown in Table 1.

(c) Light Emitting Efficiency and Emitted Color

DC voltage is applied to each device for light emission with source measure unit Model 2400 (manufactured by Toyo Corporation). The luminance at that time is measured with a luminometer BM-8 (manufactured by Topcon Corporation). Emitted color at that time is visually observed. The light emission spectrum and light emitting wavelength are measured with a spectrum analyzer PMA-11 (manufactured by Hamamatsu Photonics K.K.). On the basis of these measurements, external quantum efficiency around 1,000 cd/m$^2$ of luminance is computed according to a luminance conversion method. The value of each device is shown in Table 1 as a relative value with the value of device 1-1 of the invention being as 100. The greater the numeral, the better is the efficiency.

(d) Half Value Width

The wavelength showing relative strength of 0.5 is determined by using the light emission spectrum obtained in (c), and the difference therebetween is taken as half value width. The value of device 1-1 of the invention is taken as 100, and the relative values thereof are shown in Table 1. The smaller the half value width, the sharper is the spectrum and preferred chromaticity is obtained.

TABLE 1

| No. of Device | HTL | Light emitting Layer Material 1 | Light emitting Layer Material 2 | Light emitting Layer Material 3 | Light emitting Efficiency | Half Life Time | Light Emission Wavelength (nm) | Emitted Color | Half Value Width |
|---|---|---|---|---|---|---|---|---|---|
| Device 1-1 (Invention) | None | A (15%) | mCBP (85%) | None (0) | 100 | 100 | 464 | Blue | 100 |
| Device 1-2 (Invention) | None | B (15%) | mCBP (85%) | None (0) | 112 | 75 | 457 | Blue | 111 |
| Device 1-3 (Invention) | None | C (15%) | mCBP (85%) | None (0) | 141 | 213 | 465 | Blue | 80 |
| Device 1-4 (Invention) | None | D (15%) | mCBP (85%) | None (0) | 104 | 146 | 459 | Blue | 102 |
| Device 1-5 (Invention) | None | E (15%) | mCBP (85%) | None (0) | 99 | 103 | 466 | Blue | 101 |
| Device 1-6 (Invention) | None | F (15%) | mCBP (85%) | None (0) | 103 | 92 | 462 | Light Blue | 140 |
| Device 1-7 (Invention) | None | G (15%) | mCBP (85%) | None (0) | 97 | 101 | 468 | Blue | 75 |
| Comparative Device 1 | None | ref-1 (15%) | mCBP (85%) | None (0) | 64 | 70 | 462 | Blue | 95 |
| Comparative Device 2 | None | ref-2 (15%) | mCBP (85%) | None (0) | A device cannot be manufactured. | — | — | — | — |
| Comparative Device 3 | None | ref-3 (15%) | mCBP (85%) | None (0) | Light emission is weak. | — | 477 | Blue | 105 |
| Device 2-1 (Invention) | mCBP | C (15%) | mCBP (85%) | None (0) | 157 | 250 | 465 | Blue | 82 |

TABLE 1-continued

| No. of Device | HTL | Light emitting Layer Material 1 | Light emitting Layer Material 2 | Light emitting Layer Material 3 | Light emitting Efficiency | Half Life Time | Light Emission Wavelength (nm) | Emitted Color | Half Value Width |
|---|---|---|---|---|---|---|---|---|---|
| Device 2-2 (Invention) | HTL-1 | C (15%) | mCBP (85%) | None (0) | 167 | 201 | 465 | Blue | 84 |
| Device 2-3 (Invention) | HTL-1 | G (15%) | mCBP (85%) | None (0) | 149 | 209 | 468 | Blue | 42 |
| Device 2-4 (Invention) | HTL-2 | C (15%) | mCBP (85%) | None (0) | 169 | 217 | 465 | Blue | 80 |
| Device 3-1 (Invention) | None | C (30%) | mCBP (70%) | None (0) | 139 | 251 | 467 | Bluish green | 181 |
| Device 3-2 (Invention) | None | C (30%) | mCBP (55%) | Bn-1 (15%) | 142 | 270 | 465 | Blue | 79 |
| Device 3-3 (Invention) | None | G (30%) | mCBP (70%) | None (0) | 126 | 267 | 469 | Greenish blue | 137 |
| Device 3-4 (Invention) | None | G (30%) | mCBP (55%) | Bn-1 (15%) | 135 | 301 | 468 | Blue | 75 |
| Device 3-5 (Invention) | HTL-1 | C (30%) | mCBP (55%) | Bn-1 (15%) | 140 | 276 | 465 | Blue | 78 |

It can be seen from the results in Table 1 that the devices in the invention are excellent in light emitting efficiency and half life time is long as compared with comparative devices having similar light emitting wavelength. It is also seen that light emitting efficiency is further improved when a carbazole material is used on the anode side as the charge transporting layer.

On the other hand, when a phosphorescent material is used in high concentration, the half value width rises and color purity deteriorates, but broadening of spectrum can be restrained by the addition of a hydrocarbon material to the light emitting layer.

In the case of the displaying apparatus, it is required to instantaneously emit light in high luminance through high current density at each pixel part, and the luminescent devices of the invention can be advantageously used even in such a case, since devices are designed to be capable of obtaining high light emitting efficiency.

The structures of the compounds used in the examples and comparative examples are shown below.

While the present invention has been shown and described with reference to certain exemplary embodiments thereof, it will be understood by those skilled in the art that various changes modifications may be made therein without departing from the spirit and scope of the present invention as defined by the appended claims.

-continued

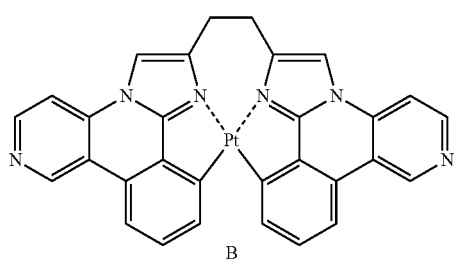

B

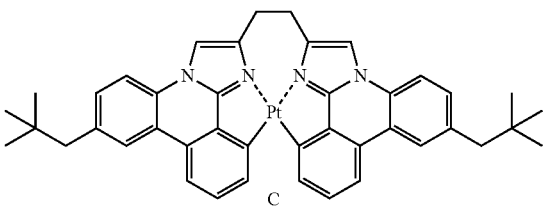

C

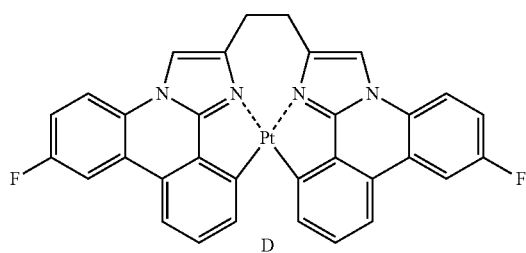

D

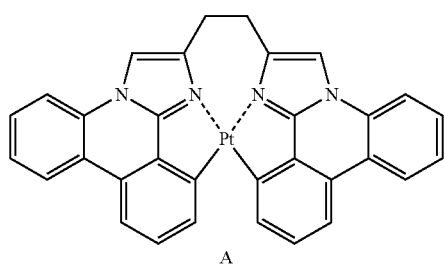

A

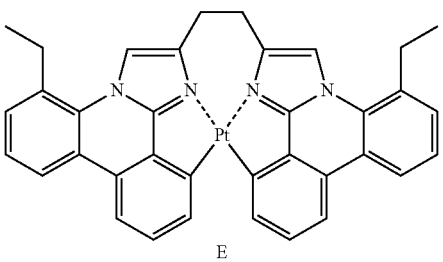

E

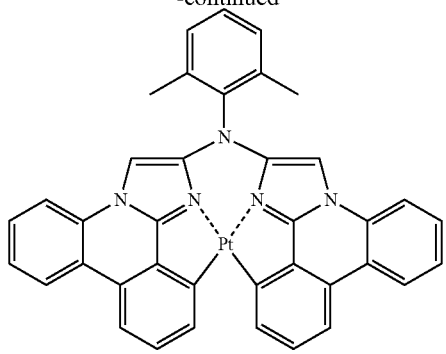
F
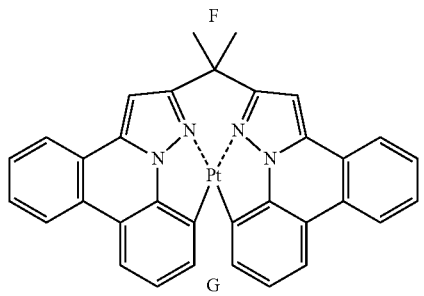
G
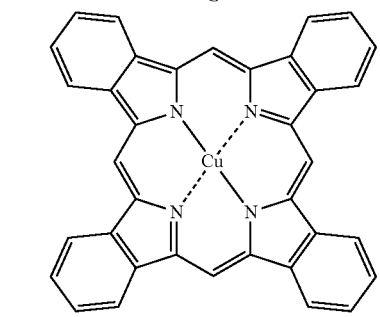
CuPc
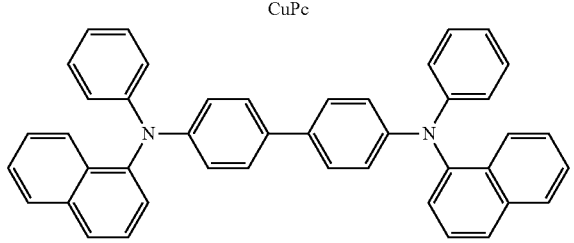
NPD
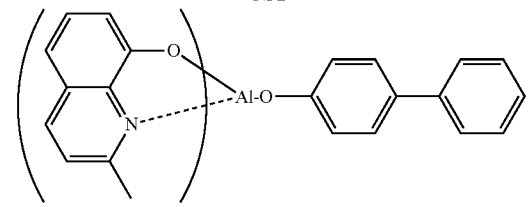
BAlq
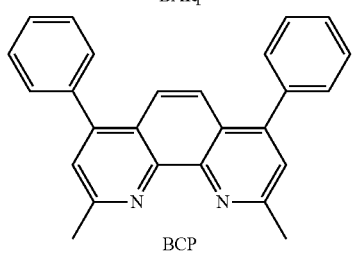
BCP
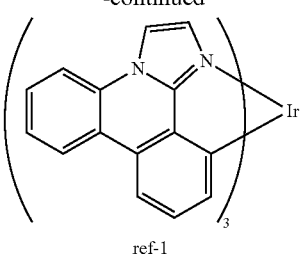
ref-1
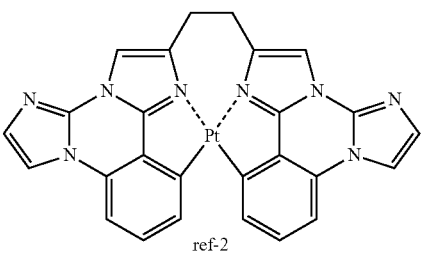
ref-2
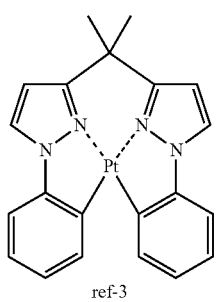
ref-3
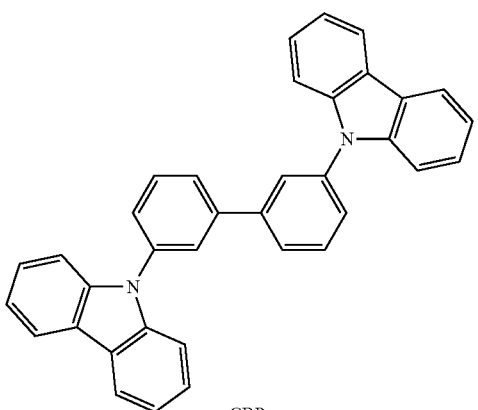
mCBP
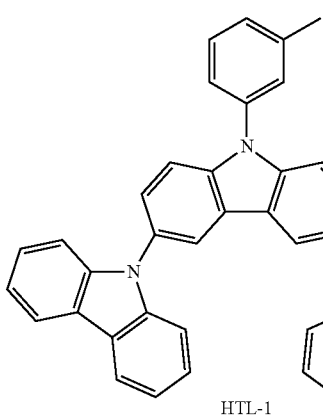
HTL-1

-continued

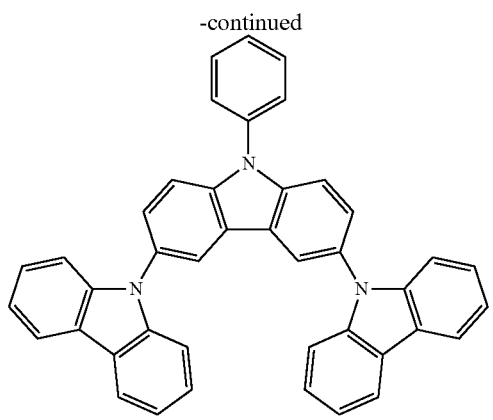

HTL-2

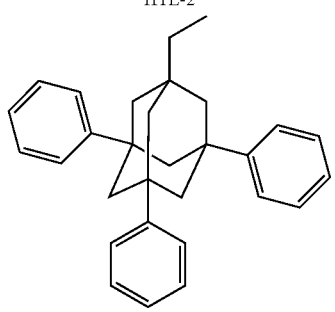

Bn-1 = (1-7)

What is claimed is:

1. A material for a light emitting device comprising a compound represented by the following formula (1):

(1)

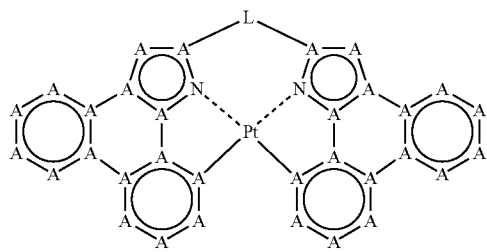

wherein each A independently represents a nitrogen atom or a carbon atom, which may have a substituent, each of the rings consisting of A and nitrogen atoms independently represents an aromatic ring or an aromatic heterocyclic ring; and
L represents a divalent linking group.

2. The material for a light emitting device according to claim 1,
wherein the compound represented by formula (1) is a compound represented by the following formula (2):

(2)

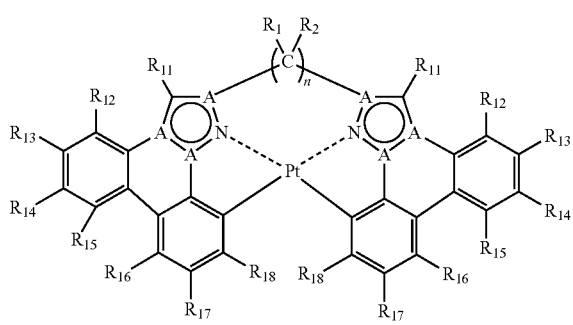

wherein each of $R_1$ and $R_2$ independently represents a hydrogen atom or a hydrocarbon group, and they may be linked to each other to form a ring;
each A independently represents a nitrogen atom or a carbon atom, a ring consisting of A, carbon atoms and nitrogen atoms represents an aromatic heterocyclic ring;
n represents an integer of 1 or 2; and
each of $R_{11}$ to $R_{18}$ independently represents a hydrogen atom or a substituent.

3. The material for a light emitting device according to claim 2,
wherein the compound represented by formula (2) is a compound represented by the following formula (3):

(3)

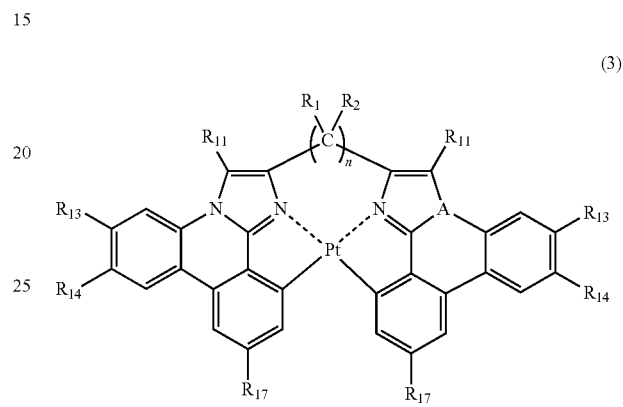

wherein each of $R_1$ and $R_2$ independently represents a hydrogen atom or a hydrocarbon group;
n represents an integer of 1 or 2; and
each of $R_{11}$, $R_{13}$, $R_{14}$ and $R_{17}$ independently represents a hydrogen atom or a substituent.

4. The material for a light emitting device according to claim 2,
wherein the compound represented by formula (2) is a compound represented by the following formula (4):

(4)

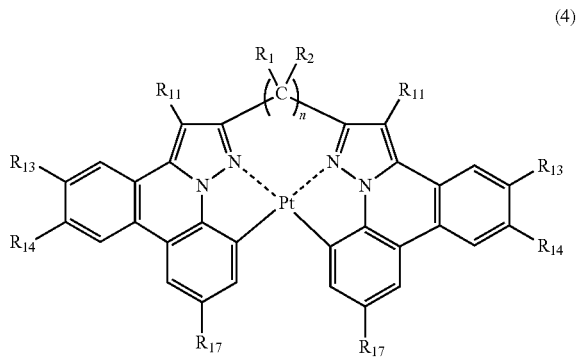

wherein each of $R_1$ and $R_2$ independently represents a hydrogen atom or a hydrocarbon group;
n represents an integer of 1 or 2; and
each of $R_{11}$, $R_{13}$, $R_{14}$ and $R_{17}$ independently represents a hydrogen atom or a substituent.

5. The material for a light emitting device according to claim 2,
wherein at least one of $R_{12}$ to $R_{18}$ in formula (2) represents a hydrocarbon group having 1 to 10 carbon atoms.

6. An organic electroluminescence device comprising:

a pair of electrodes; and an organic layer including a light emitting layer between the pair of electrodes, wherein the organic layer contains the compound represented by any of formulae (1) to (4) according to claim 1.

7. The organic electroluminescence device according to claim 6, wherein the layer containing the compound represented by formula (1) is the light emitting layer.

8. The organic electroluminescence device according to claim 6, wherein the light emitting layer further contains a hydrocarbon compound.

9. The organic electroluminescence device according to claim 8, wherein the hydrocarbon compound is a compound represented by the following formula (VI):

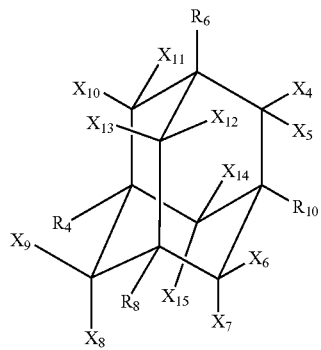

(VI)

wherein each of $R_4$, $R_6$, $R_8$, $R_{10}$, $X_4$ to $X_{15}$ independently represents a hydrogen atom or a substituent.

10. The organic electroluminescence device according to claim 6, wherein the electrodes include an anode, a charge transporting layer is provided between the light emitting layer and the anode, and the charge transporting layer contains a carbazole compound.

11. The organic electroluminescence device according to claim 10, wherein the carbazole compound is represented by the following formula (a):

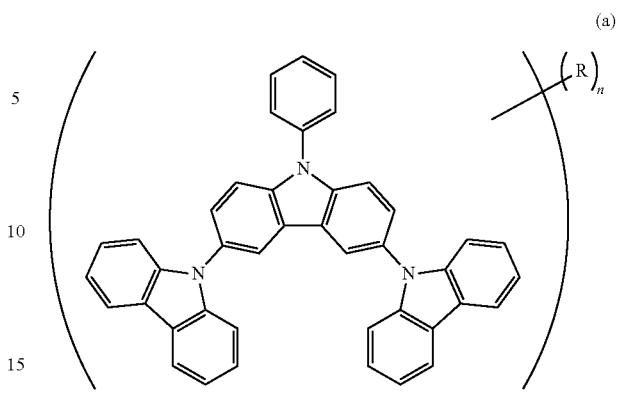

(a)

wherein R represents a substituent capable of substituting on the hydrogen atom of the compound;

when there are two or more R's, each R may be the same with or different from every other R; and n represents an integer of 0 to 8.

12. The organic electroluminescence device according to claim 10, wherein the carbazole compound is represented by the following formula (b):

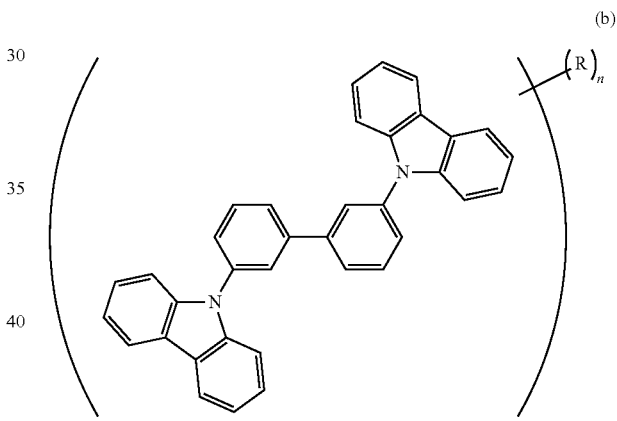

(b)

wherein R represents a substituent capable of substituting on the hydrogen atom of the compound;

when there are two or more R's, each R may be the same with or different from every other R; and n represents an integer of 0 to 8.

13. A display using the organic electroluminescence device according to claim 6.

14. An illuminating apparatus using the organic electroluminescence device according to claim 6.

* * * * *